United States Patent
Aho et al.

(10) Patent No.: US 10,779,732 B2
(45) Date of Patent: Sep. 22, 2020

(54) SYSTEMS AND METHODS FOR ASSESSING PROPERTIES OF BIOLOGICAL TUBES

(71) Applicant: Mayo Foundation For Medical Education and Research, Rochester, MN (US)

(72) Inventors: Johnathon M. Aho, Rochester, MN (US); Dennis A. Wigle, Rochester, MN (US); Matthew W. Urban, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 782 days.

(21) Appl. No.: 15/466,227

(22) Filed: Mar. 22, 2017

(65) Prior Publication Data

US 2017/0281006 A1   Oct. 5, 2017

Related U.S. Application Data

(60) Provisional application No. 62/314,563, filed on Mar. 29, 2016.

(51) Int. Cl.
*A61B 5/02* (2006.01)
*G01L 1/16* (2006.01)
*A61B 5/00* (2006.01)

(52) U.S. Cl.
CPC ........ *A61B 5/0053* (2013.01); *A61B 5/02007* (2013.01); *A61B 5/42* (2013.01);
(Continued)

(58) Field of Classification Search
CPC ..... A61B 5/0053; A61B 5/02007; A61B 5/42; A61B 5/4233; A61B 5/687; A61B 5/6876;
(Continued)

(56) References Cited

U.S. PATENT DOCUMENTS 3,480,003 A      11/1969   Crites
5,235,989 A  *  8/1993   Zomer ................ A61B 5/1135
                                                              600/534
(Continued)

OTHER PUBLICATIONS

Aho, J., et al., Nondestructive Measurement of Esophageal Biaxial Mechanical Properties Utilizing Sonometry, Phys Med Biol. Jul. 7, 2016; 61(13): 4781-4795.
(Continued)

*Primary Examiner* — Navin Natnithithadha
(74) *Attorney, Agent, or Firm* — Quarles & Brady LLP

(57) ABSTRACT

A system and method is provided for measuring a mechanical property of a biological tube. The system and method operate to arrange a plurality of piezoelectric elements about the biological tube and apply a predetermined force or transduce an endogeneous or exogeneous force to the biological tube. The system and method also operate to receive a respective signal from each piezoelectric element in the plurality of piezoelectric elements responsive to the application of the predetermined force or a transduced endogenous or exogeneous force and calculate the mechanical property of the biological tube based on the signals received from the plurality of piezoelectric elements.

15 Claims, 16 Drawing Sheets

(52) U.S. Cl.
CPC ............ *A61B 5/4233* (2013.01); *A61B 5/687* (2013.01); *A61B 5/6876* (2013.01); *A61B 5/7271* (2013.01); *G01L 1/16* (2013.01); *A61B 2562/0261* (2013.01); *G01N 2203/0089* (2013.01); *G01N 2203/0274* (2013.01); *G01N 2203/0623* (2013.01)

(58) Field of Classification Search
CPC .......... A61B 5/7271; A61B 2562/0261; A61B 5/0048; A61B 5/4222; G01L 1/16; G01N 2203/0089; G01N 2203/0274; G01N 2203/0623
USPC ................................................. 600/587, 593
See application file for complete search history.

(56) References Cited

U.S. PATENT DOCUMENTS

| | | | |
|---|---|---|---|
| 5,398,689 A | 3/1995 | Connor | |
| 5,513,639 A | 5/1996 | Satomi | |
| 6,097,984 A | 8/2000 | Douglas | |
| 6,740,047 B2 | 5/2004 | Holmes | |
| 7,628,753 B2 | 12/2009 | Rabinovitz | |
| 7,647,831 B2* | 1/2010 | Corcoran | A61B 5/0215 73/700 |
| 7,708,705 B2 | 5/2010 | Iddan | |
| 7,857,767 B2* | 12/2010 | Ferren | A61M 25/0116 600/481 |
| 7,966,886 B2* | 6/2011 | Corcoran | A61B 5/0031 73/700 |
| 8,000,784 B2* | 8/2011 | Ferren | A61M 25/0116 607/2 |
| 8,019,413 B2* | 9/2011 | Ferren | A61B 1/00156 607/2 |
| 8,024,036 B2* | 9/2011 | Ferren | A61B 1/00156 607/2 |
| 8,083,665 B2* | 12/2011 | Dlugos | A61F 5/005 600/37 |
| 8,212,552 B2 | 7/2012 | Gianchandani | |
| 8,231,538 B2* | 7/2012 | Aebersold | A61B 5/0215 600/485 |
| 8,512,219 B2* | 8/2013 | Ferren | A61B 1/00156 600/12 |
| 8,660,642 B2* | 2/2014 | Ferren | A61B 1/00156 607/2 |
| 8,694,092 B2* | 4/2014 | Ferren | A61B 1/00156 607/2 |
| 8,920,307 B2* | 12/2014 | Marcotte | A61F 5/005 600/37 |
| 9,198,563 B2* | 12/2015 | Ferren | A61B 1/041 |
| 9,408,530 B2* | 8/2016 | Ferren | A61B 1/041 |
| 9,801,527 B2* | 10/2017 | Ferren | A61B 1/00156 |
| 9,968,790 B2* | 5/2018 | Toth | A61B 5/042 |
| 10,226,633 B2* | 3/2019 | Toth | A61B 5/042 |
| 2007/0156211 A1* | 7/2007 | Ferren | A61M 25/0116 607/101 |
| 2007/0163353 A1* | 7/2007 | Lec | A61B 5/0215 73/700 |
| 2007/0225576 A1 | 9/2007 | Brown | |
| 2007/0225633 A1* | 9/2007 | Ferren | A61M 25/0116 604/27 |
| 2007/0244520 A1* | 10/2007 | Ferren | A61B 1/00156 607/2 |
| 2008/0033569 A1* | 2/2008 | Ferren | A61B 34/20 623/23.7 |
| 2008/0103440 A1* | 5/2008 | Ferren | A61B 1/00156 604/95.01 |
| 2008/0208065 A1* | 8/2008 | Aebersold | A61B 5/0215 600/488 |
| 2009/0131737 A1* | 5/2009 | Ferren | A61B 1/00156 600/12 |
| 2009/0131738 A1* | 5/2009 | Ferren | A61B 1/00156 600/12 |
| 2010/0152532 A1* | 6/2010 | Marcotte | A61F 5/005 600/37 |
| 2010/0241000 A1* | 9/2010 | Kondo | A61B 5/02007 600/454 |
| 2011/0275880 A1* | 11/2011 | Ferren | A61B 1/00156 600/12 |
| 2012/0035434 A1* | 2/2012 | Ferren | A61B 1/00156 600/301 |
| 2012/0035437 A1* | 2/2012 | Ferren | A61B 1/041 600/302 |
| 2012/0035438 A1* | 2/2012 | Ferren | A61B 1/041 600/302 |
| 2012/0035439 A1* | 2/2012 | Ferren | A61B 1/041 600/302 |
| 2012/0035440 A1* | 2/2012 | Ferren | A61B 1/041 600/302 |
| 2012/0035540 A1* | 2/2012 | Ferren | A61B 1/041 604/95.01 |
| 2012/0041291 A1* | 2/2012 | Ferren | A61B 1/041 600/365 |
| 2012/0053666 A1* | 3/2012 | Ferren | A61B 1/00156 607/119 |
| 2013/0090573 A1 | 4/2013 | Shaker | |
| 2015/0224326 A1* | 8/2015 | Toth | A61B 5/042 600/301 |
| 2017/0027424 A1* | 2/2017 | Ferren | A61B 1/041 |

OTHER PUBLICATIONS

Walker, W.F., et al., "A fundamental limit on delay estimation using partially correlated speckle signals," IEEE Trans. Ultrason. Ferroelectr. Freq. Control, vol. 42, pp. 301-308, 1995.

Hasegawa H., et al., "Improving accuracy in estimation of artery-wall displacement by referring to center frequency of RF echo," IEEE Trans. Ultrason. Ferroelectr. Freq. Control, vol. 53, pp. 52-63, 2006.

Bernal, M., et al., "Measurement of biaxial mechanical properties of soft tubes and arteries using piezoelectric elements and sonometry," Phys. Med. Biol., vol. 56, p. 3371, 2011.

Yang, W., et al., "3D Mechanical properties of the layered esophagus: experiment and constitutive model.," J. Biomech. Eng., vol. 128, No. 6, pp. 899-908, Dec. 2006.

Gregersen, H., et al., "Determination of homeostatic elastic moduli in two layers of the esophagus.," J. Biomech. Eng., vol. 130, No. 1, p. 011005, Feb. 2008.

Sjöqvist, S., et al., "Experimental orthotopic transplantation of a tissue-engineered oesophagus in rats.," Nat. Commun., vol. 5, p. 3562, Jan. 2014.

Jensen, T., et al"Biomimetic and synthetic esophageal tissue engineering.," Biomaterials, vol. 57, pp. 133-141, Jul. 2015.

Hur, C., et al., "Trends in esophageal adenocarcinoma incidence and mortality," Cancer, vol. 119, No. 6, pp. 1149-1158, 2013.

Yoshida, N., et al., "Risk factors for pulmonary complications after esophagectomy for esophageal cancer," Surg. Today, vol. 44, No. 3, pp. 526-532, 2014.

Metzger, R., et al., "High volume centers for esophagectomy: what is the number needed to achieve low postoperative mortality?," Dis. Esophagus, vol. 17, No. 4, pp. 310-314, Jan. 2004.

Bailey, S. H., et al., "Outcomes after esophagectomy: a ten-year prospective cohort.," Ann. Thorac. Surg., vol. 75, No. 1, pp. 217-222; discussion 222, Jan. 2003.

Blencowe, N. S., et al., "Reporting of short-term clinical outcomes after esophagectomy: a systematic review.," Ann. Surg., vol. 255, No. 4, pp. 658-666, Apr. 2012.

Fan, Y., et al., "A two-layered mechanical model of the rat esophagus. Experiment and theory.," Biomed. Eng. Online, vol. 3, No. 1, p. 40, Nov. 2004.

Liao, D., et al., "Stress distribution in the layered wall of the rat oesophagus.," Med. Eng. Phys., vol. 25, No. 9, pp. 731-738, Nov. 2003.

Lu, X., et al., "Regional distribution of axial strain and circumferential residual strain in the layered rabbit oesophagus," J. Biomech., vol. 34, No. 2, pp. 225-233, Feb. 2001.

(56) References Cited

OTHER PUBLICATIONS

Yang, W., et al., "Directional, regional, and layer variations of mechanical properties of esophageal tissue and its interpretation using a structure-based constitutive model.," J. Biomech. Eng., vol. 128, No. 3, pp. 409-418, Jun. 2006.
Totonelli, G., et al., "Esophageal tissue engineering: a new approach for esophageal replacement.," World J. Gastroenterol., vol. 18, No. 47, pp. 6900-6907, Dec. 2012.
Bhrany, A.D., et al., "Development of an esophagus acellular matrix tissue scaffold.," Tissue Eng., vol. 12, No. 2, pp. 319-330, Feb. 2006.
Ozeki, M., et al., "Evaluation of decellularized esophagus as a scaffold for cultured esophageal epithelial cells.," J. Biomed. Mater. Res. A, vol. 79, No. 4, pp. 771-778, Dec. 2006.
Sokolis, D. P., et al., "Strain-energy function and three-dimensional stress distribution in esophageal biomechanics.," J. Biomech., vol. 43, No. 14, pp. 2753-2764, Oct. 2010.
Stavropoulou, E. A., et al., "Biomechanical and histological characteristics of passive esophagus: experimental investigation and comparative constitutive modeling.," J. Biomech., vol. 42, No. 16, pp. 2654-2563, Dec. 2009.
Sommer, G., et al., "Multiaxial mechanical response and constitutive modeling of esophageal tissues: Impact on esophageal tissue engineering.," Acta Biomater., vol. 9, No. 12, pp. 9379-9391, Dec. 2013.

\* cited by examiner

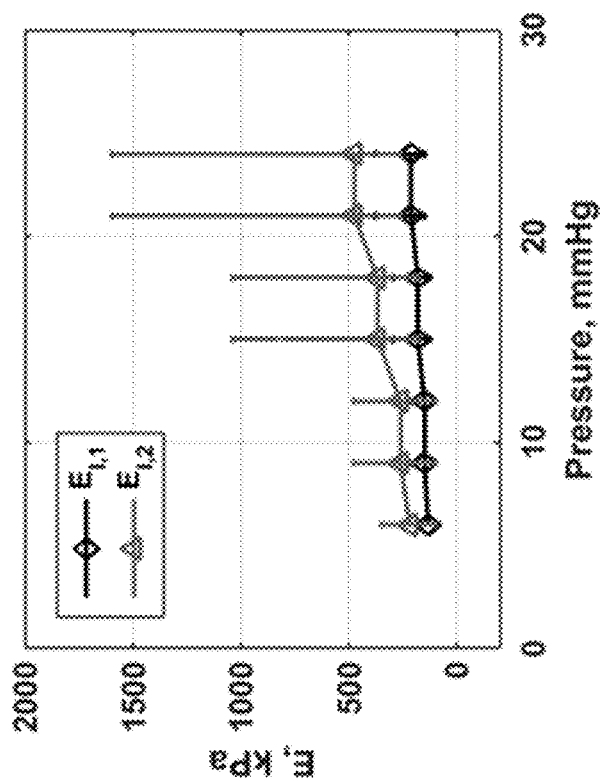
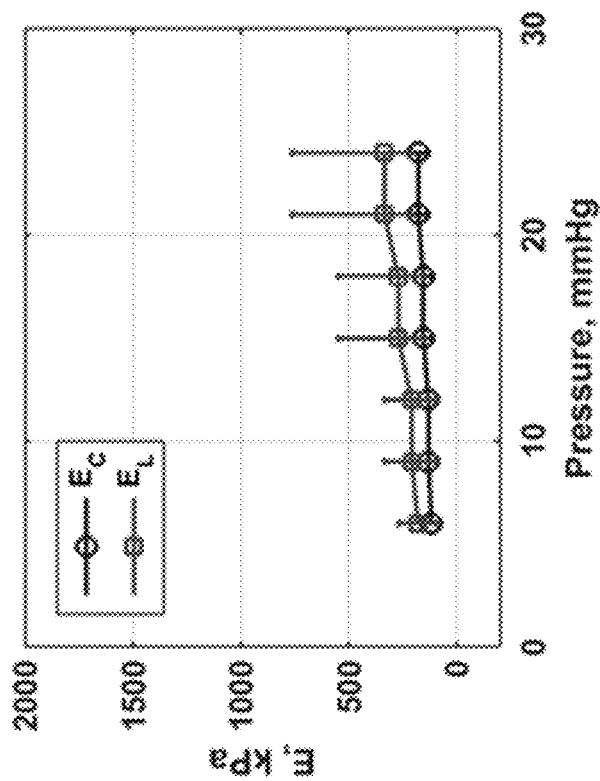
Fig. 10A
Fig. 10B

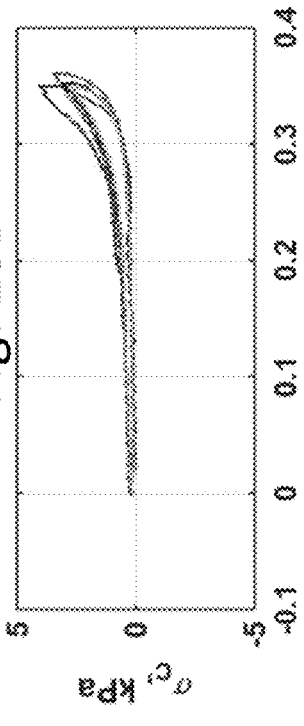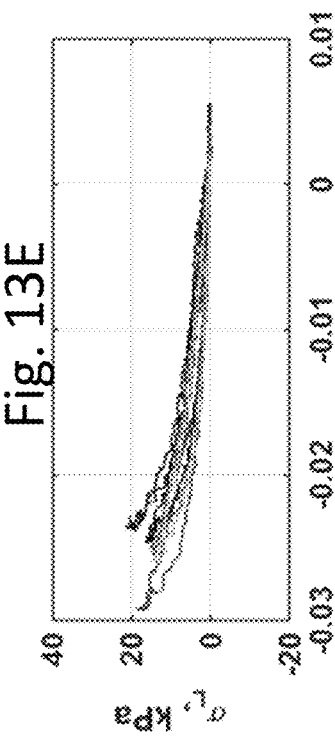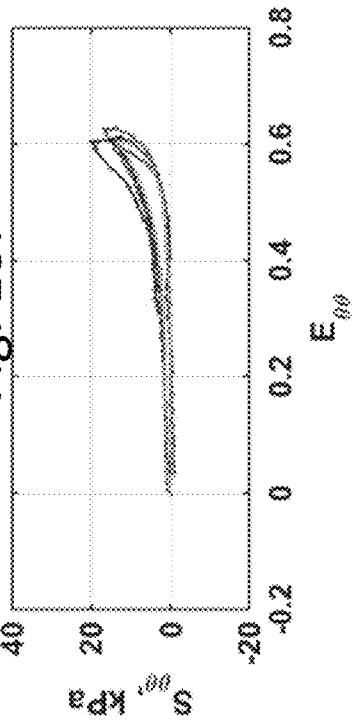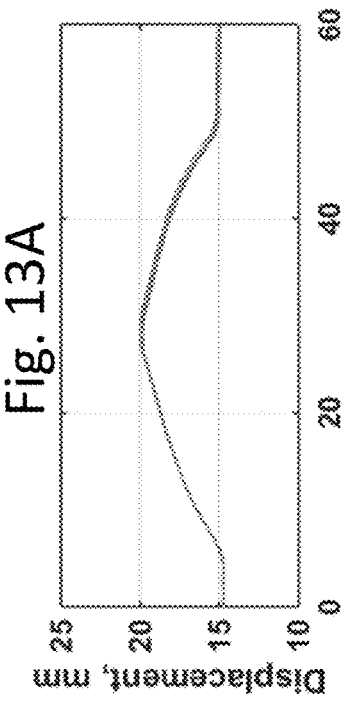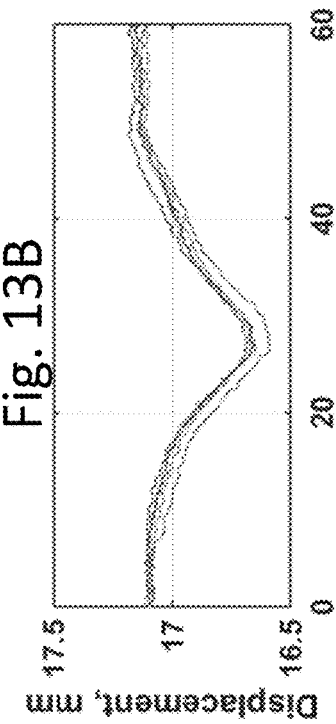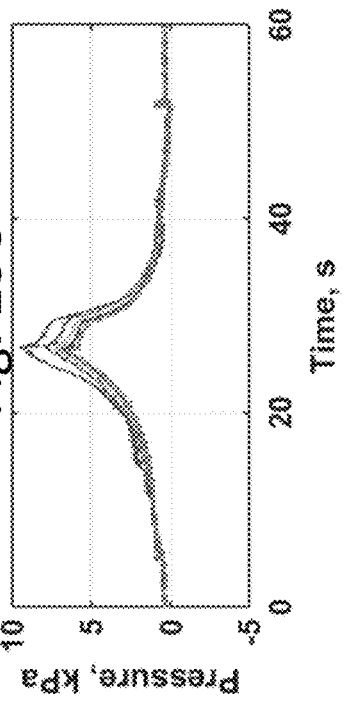

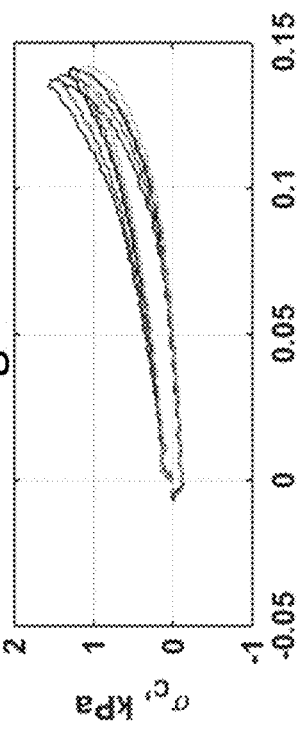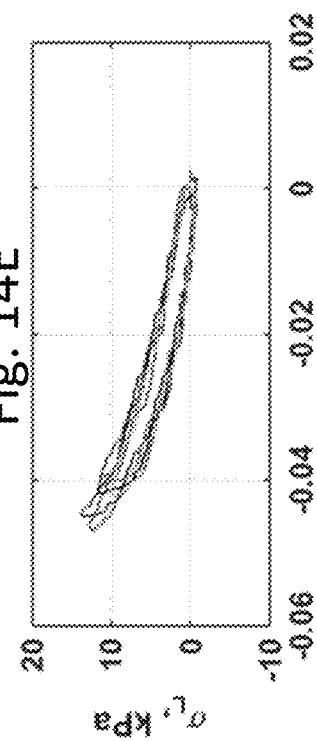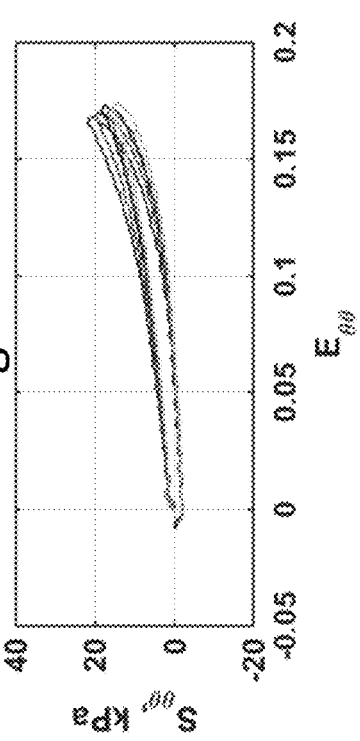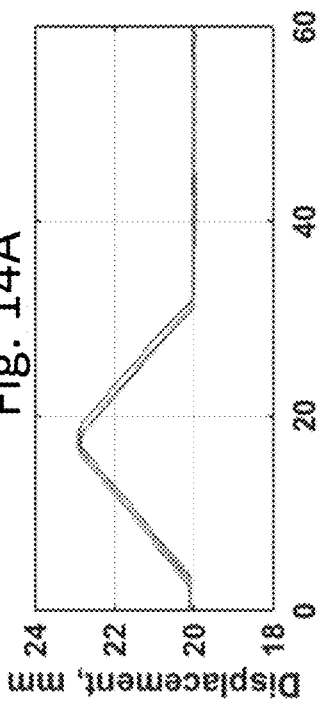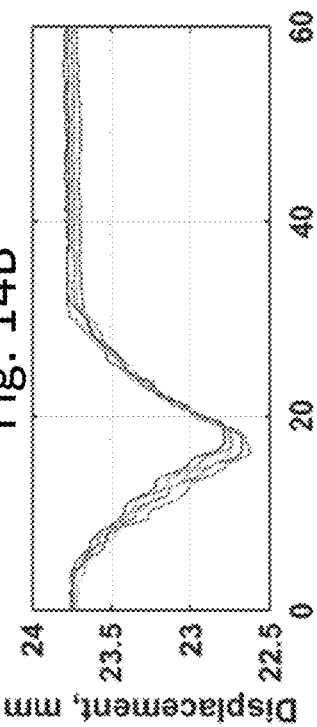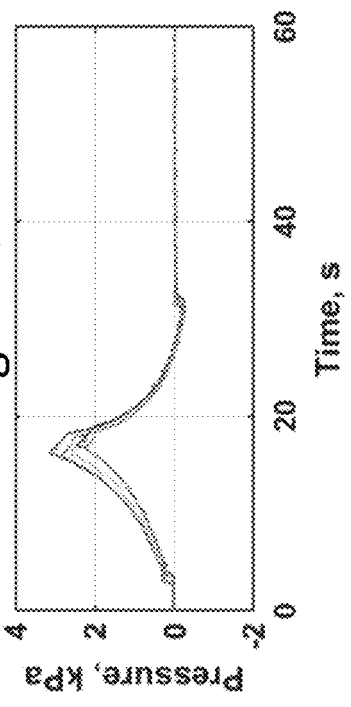

SYSTEMS AND METHODS FOR ASSESSING PROPERTIES OF BIOLOGICAL TUBES

CROSS-REFERENCE TO RELATED APPLICATIONS

This application is based on, claims priority to, and incorporates herein by reference in its entirety, U.S. Provisional Application Ser. No. 62/314,563, filed Mar. 29, 2016, and entitled "SYSTEMS AND METHODS FOR ASSESSING PROPERTIES OF BIOLOGICAL TUBES."

STATEMENT REGARDING FEDERALLY SPONSORED RESEARCH

This invention was made with government support under HL105355 awarded by the National Institutes of Health. The government has certain rights in the invention.

BACKGROUND

The body and its processes rely on anatomical compartmentalization to provide homeostasis and to function properly. A particular compartment type that is ubiquitous throughout the human body and other mammals is the biological tube. For example, biological tubes are part of the vascular system, the gastrointestinal system, and many other systems. In a variety of pathological states the mechanical properties of these tubes may be affected. For example in the vascular system, atherosclerotic disease may cause a thickening or stiffening of the blood vessel as well as local fibrotic or other structural changes. In the gastrointestinal system (GI), dysmotility disorders of the gastrointestinal tract may result in the tubular structure becoming hypo- or hyper-kinetic, and malignant or benign disorders may include a pathological thickening of the structure.

Pathological states of hollow organs commonly affect the organs' mechanical properties. Malignancy may stiffen a tubular structure both at the site of malignancy itself and at areas in proximity to the site through local inflammation and proliferation of tissue growth, for example. Additionally, dysmotility syndromes may affect portions of the gastrointestinal tract and thereby disturb both the functioning and mechanical properties. These pathologies are difficult to diagnose through available methods because the current known techniques do not provide specificity regarding, for example, location or distribution.

More particularly as an example, the purpose of the esophagus is to provide a conduit that regulates the movement of a food bolus (i.e., a chewed mass of food ready for swallowing) into the upper gastrointestinal tract. This is accomplished by the esophagus moving the bolus toward the stomach using peristalsis, which is the coordinated action of nerve and muscle tissue propelling the bolus through the esophagus to the stomach. These processes may be disrupted leading to esophageal motility disorders. Current diagnoses of these disorders are accomplished through manometry. Manometers are organized on a single straight tube using either balloons connected to sensors or sensors directly on the tube which monitor pressure which is then inserted down the esophagus to monitor changes in esophageal pressure during peristalsis. Using this type of monitoring for dysfunctional portions of the esophagus is subpar, as dysfunction segments are mapped to a single point (length down catheter) and the pressure generated at this point is a composite measure of the three dimensional structure and may either miss, or incorrectly map pathology to a location.

Therefore, it would be desirable to have a system and method allowing for the enhanced measurement of the mechanical properties of a biological tube within a subject which may provide improved diagnoses for tubular disorders.

SUMMARY

The present disclosure provides a system and method for enhancing the measurement of the mechanical characteristics of a biological tube within a subject. The systems and methods provided herein utilize, for example, displacement of sonometric crystals to determine displacement in three dimensions to determine where in three dimensional space longitudinally (proximal to distal) and radially a given biological tube pathology lies. As a non-limiting example, disorders of the vascular and gastrointestinal systems within the body may cause mechanical aberrations within the tubular structures of those systems. The mechanical characteristics of a tubular structure may be measured to determine whether any of these aberrations exist and the extent to which they may be affecting the tubular structure and surrounding systems. Piezoelectric sensors may be embedded in an array and placed internally or externally at a measurement site of the tubular structure of interest. A known force or stress may be applied or delivered to the site by a pressure vessel, such as a balloon. The force or stress that is applied may also be endogenous, swallowing or peristalsis, or exogenous as in the aforementioned balloon. Also, the force or stress may be known or transduced in some manner. The combined system of the applied force and pressure sensor measurements may be quantified and analyzed. The mechanical characteristics analyses that this system enables may lead to improved diagnoses of pathological states for tubular structures in the body.

In one configuration, a system is provided for measuring mechanical properties of a biological tube extending along an axis. The system includes a tubular substrate dimensioned to extend along the axis of the biological tube and engage the biological tube and an array of piezoelectric elements engaging the tubular substrate. The system also includes a pressure device configured to apply a fixed or variable but transduced predetermined force or stress to the biological tube and be sensed by the array when the array is engaged with the biological tube, wherein each piezoelectric element is configured to generate a signal in response to sensing application of the predetermined force. The force could also be transduced, caused by an endogenous or exogenous force, stress, or an induced pressure or motion. The system further includes a processor configured to receive the signal from at least two piezoelectric elements of the array and calculate a mechanical property of the biological tube based on signals received from the at least two piezoelectric elements in the array.

In another configuration, a method is provided for measuring a mechanical property of a biological tube. The method includes arranging a plurality of piezoelectric elements about the biological tube and applying a fixed or variable but transduced predetermined force or stress to the biological tube. The force or stress could also be transduced from an endogenously or exogenously applied force. The method also includes receiving a respective signal from each piezoelectric element in the plurality of piezoelectric elements responsive to the application of the stress and calculating the mechanical property of the biological tube based on the signals received from the plurality of piezoelectric elements.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 10A provides a graph showing the variation of the moduli with pressure using the transverse isotropic model in accordance with the present disclosure.

FIG. 10B provides a graph showing the variation of the moduli with pressure using the isotropic model in accordance with the present disclosure.

FIG. 13A is a graph showing circumferential displacement measurements from one composite esophageal sample.

FIG. 13B is a graph showing longitudinal displacement measurements from one composite esophageal sample.

FIG. 13C is a graph showing pressure measurements from one composite esophageal sample.

FIG. 13D is a graph showing circumferential stress and strain curves from one composite esophageal sample.

FIG. 13E is a graph showing longitudinal stress and strain curves from one composite esophageal sample.

FIG. 13F is a graph showing circumferential Kirchoff stress and Green's strain from one composite esophageal sample.

FIG. 14A is a graph showing circumferential displacement measurements from five repeated measurements from one mucosa-submucosa sample.

FIG. 14B is a graph showing longitudinal displacement measurements from five repeated measurements from one mucosa-submucosa sample.

FIG. 14C is a graph showing pressure measurements from five repeated measurements from one mucosa-submucosa sample.

FIG. 14D is a graph showing circumferential stress and strain curves from five repeated measurements from one mucosa-submucosa sample.

FIG. 14E is a graph showing longitudinal stress and strain curves from five repeated measurements from one mucosa-submucosa sample.

FIG. 14F is a graph showing circumferential Kirchoff stress and Green's strain from five repeated measurements from one mucosa-submucosa sample.

DETAILED DESCRIPTION

The present disclosure provides systems and method that can apply a force or stress to deform a hollow, tubular organ, and track or measure the displacement induced by that stress to evaluate the mechanical properties of the tubular organ. The force or stress may be endogenous or exogenous. In one non-limiting example, piezoelectric sensors may be used to measure pressure or force. More particularly, to perform those manipulations and measurements on a biological tube or organ, the present disclosure may use an array of piezoelectric crystals. The array may be incorporated in or attached to a sleeve, membrane, or distensible structure that may be positioned around, on the surface of, or within the tubular organ. The piezocrystals may be attached within a mesh or on the surface of the mesh, by sutures or other fixation method, or embedded in the sleeve.

External pressure may be applied within a closed compliant tube where piezocrystals are mounted on the interior or exterior of that tube. Non-limiting clinical applications may include the esophagus or any other segment of the gastrointestinal (GI) tract or vasculature.

In another aspect of the disclosure, the tube with the piezocrystals may be hollow for some applications, such as applications involving the arteries or veins. In this case, for example, spherical piezocrystals may be encased in the compliant hollow tube. A pressure sensor may be incorporated to monitor the pressure in real-time applications. The applied pressure may be static or dynamic. Alternatively as another non-limiting example, a static baseline may be established, and then a dynamic pressure variation may be applied.

Figure 1:
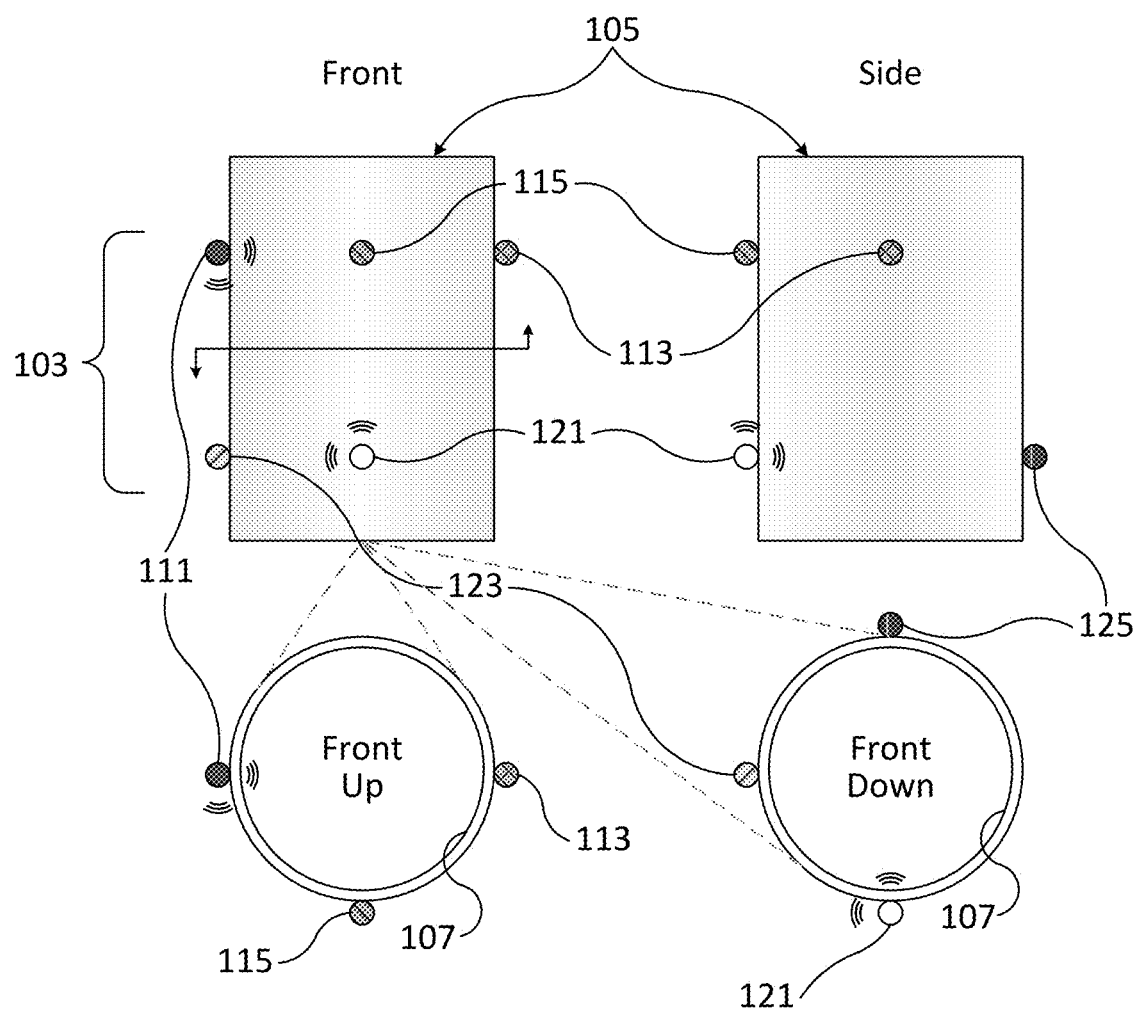
FIG. 1 is a schematic diagram illustrating some example locations of piezoelectric sensors within an array in accordance with the present disclosure.

Turning to FIG. 1, an array of piezocrystals 103 may be arranged about a tubular substrate 105 to measure displacements in multiple directions, such as the longitudinal and circumferential directions. The tubular substrate 105 may be hollow and may include a lumen 107 configured to receive a biological tube. Multiple unique transmitters 111, 121 may be placed at different levels along the longitudinal direction of the tubular substrate 105. For each of the transmitters 111, 121, there may be multiple unique receivers 113, 115, 123, 125 that, as will be described, may be used to measure the diameter and length and changes thereto of a tubular organ engaged with the tubular substrate 105.

Figure 2:
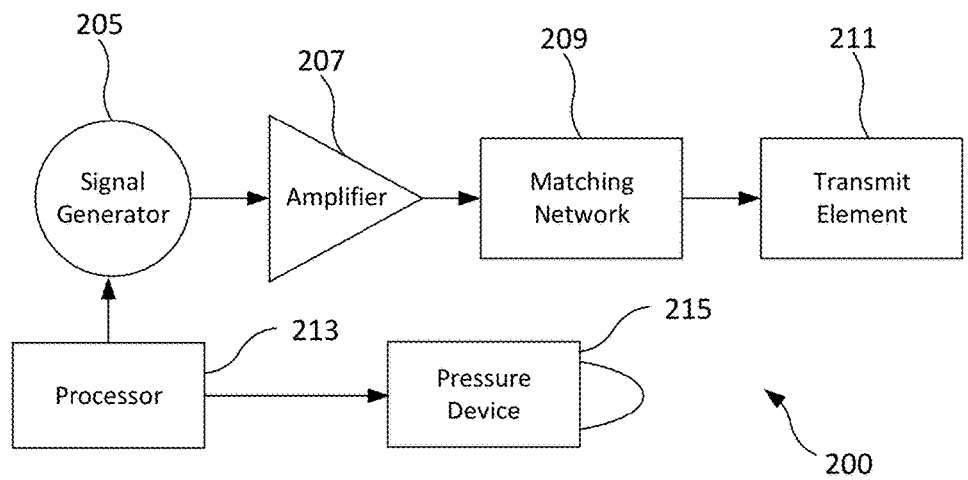
FIG. 2 is a block diagram of an example signal transmission chain including a signal generator, amplifier, matching network, and transmit piezocrystal in accordance with the present disclosure.

Each transmitter 111, 121 of FIG. 1 may be driven, as a non-limiting example, using drive circuit 200, as illustrated in FIG. 2. The drive circuit 200 may include, as a non-limiting example, a signal generator 205, an amplifier 207, a matching network 209, and, ultimately, a transmit element 211, which may be a transmit piezocrystal. Each transmitter 111, 121 may be controlled by a processor 213 and excited with an unencoded signal, such as a harmonic signal, with a sinusoidal signal, or with a coded signal. The transmitted signals may be emitted at a rate known as the pulse repetition frequency (PRF). The system of FIG. 2 may also include, as a non-limiting example, a pressure device 215 configured to apply a predetermined force or transduce an applied endogenous or exogenous force to a biological tube that will then be sensed by an array when the array is engaged with the biological tube. The biological tube may be one of a section of a gastrointestinal tract, an artery, a vein, or any other relevant biological tube.

Figure 3:
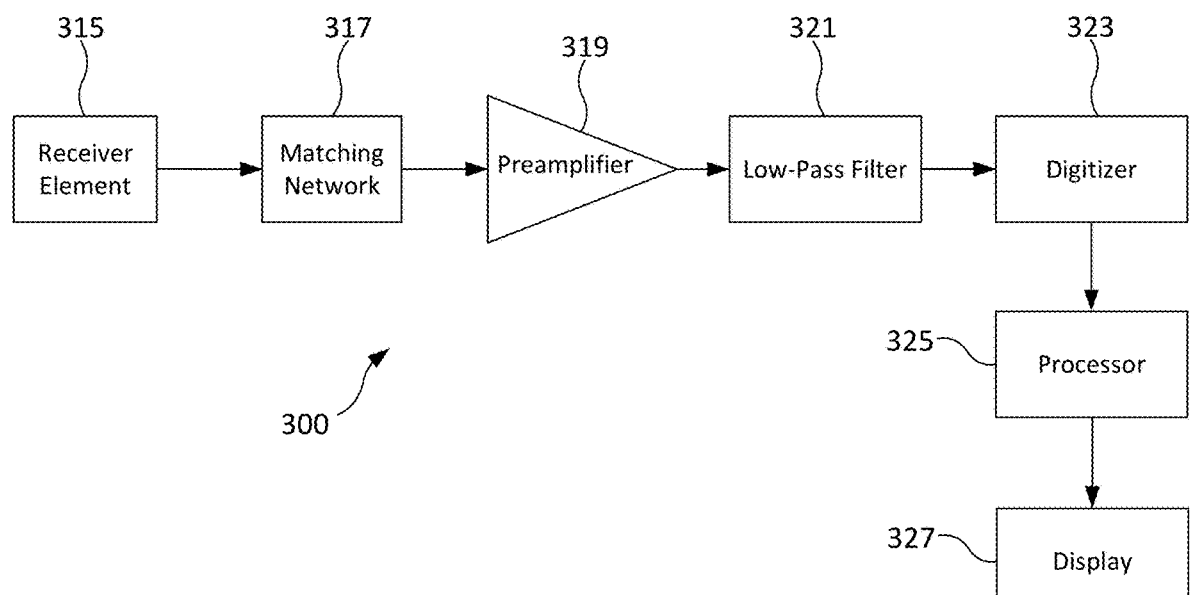
FIG. 3 is a block diagram of an example signal receiving chain including a receiver element, matching network, amplifier, filter, and digitizer in accordance with the present disclosure.

More particularly, referring to FIG. 3, a receiver circuit 300 may include a receiver element 315 configured to monitor and receive signals and a matching network 317. The received signal may be conditioned with a preamplifier 319 and filtered with an active or passive bandpass or low-pass filter 321. The conditioned signal may then be digitized by a digitizer 323 for further analysis. If the transmitter 111, 121 was driven by a coded signal, the digitized signals may be processed with a matched or mismatched filter. The received and processed signals may then be provided to a processor 325 to perform desired analysis and calculate one or more mechanical properties of a biological tube coupled to the transmitter 111, 121. Thus, as will be described, the mechanical properties may include a variety of different properties and may be formed into a report that is generated by the processor 325. In some configurations, the processor 213 of FIG. 2 and the processor 325 of FIG. 3 may be the same processor.

In particular, the signals acquired by the above-described systems may be processed by the processor 325 using upsampling and a normalized cross-correlation to find relative time differences, Δt. The relative time difference may be found by finding the peak of the normalized cross-correlation function. The processors 213, 325, described above, may use these time differences to calculate the change in distance, Δd, between the transmitters 111, 121 and the receiving piezocrystal 113, 115, 123, 125 using the relationship Δd=cΔt, where c is the speed of sound in the fluid and is assumed to be a constant. To extract the motion of the biological tube from the signals, a cross-correlation algorithm may be used to determine the time delays between consecutive signals. Before the cross-correlation is performed, the samples may be up-sampled by a factor of 5 to 500 MHz (or suitable sampling frequency). The normalized cross-correlation of consecutively acquired signals may be performed and the time delay associated with the peak of the normalized cross-correlation may be used to estimate the motion. These time delays may be converted to displacement by using:

$$\Delta d_n = c\Delta t_n; \tag{1}$$

$$d_n = d_0 + \sum_{i=1}^{n} \Delta d_n; \tag{2}$$

where $\Delta d_n$ is the incremental displacement estimated between signal acquisitions, c is the speed of sound in the fluid, $\Delta t_n$ is the time delay estimated between signal acquisitions, and $d_0$ is the initial length. With the 500 MHz sampling frequency, for example, the displacement resolution may be 3.08 μm assuming that c=1540 m/s. For each sample the initial distance between a given transmitter 111 and receiver 113 may be measured with a calipers to obtain initial distances, $d_0$, for strain calculations or measured using a calibrated time-of-flight method. Over the course of several seconds while the data may be acquired, pressure may be applied or normal peristalsis or pulse wave motion will move the piezocrystals. Alternatively, instead of an applied pressure, a pulse wave motion or normal peristalsis in the esophagus, for example, may be used to move the piezoelectric elements. The motion may be extracted using the procedure described above.

The arrangement of the piezoelectric elements in the array 103 as shown in FIG. 1 may allow for redundant measurements of the diameter and longitudinal motion. These redundant measurements may be averaged in a weighted or non-weighted sense depending on the received signal amplitude.

To control signal interference and control against confusion between multiple transmitters 111, 121, the processor 213, 325 may coordinate the acquisitions using an offset in time, such as offsetting by $T_{prf}/2$ where $T_{prf}=1/PRF$ and transmitters 111 and 121 may alternate transmitting signals. The PRF may be chosen in order to make measurements with sufficient time resolution to capture peristaltic motion, swallowing, or pulsatile motion. Additionally, if limited receiver channels are available, time offsets may be established for the recording of signals from different receiver piezocrystals.

The distances determined by the processor 213, 325 may then be converted into strain measurements using the following process for analyzing the radial and longitudinal strain. That is, a report may be generated by the processor that includes such information. For example, the processor 325 of FIG. 3 may use a model to compute the circumferential and longitudinal moduli and display this information via a display 327 or other feedback system, which may include physical printing systems or networked communications devices, including phones or tablets. One non-limiting example of a model includes M. Bernal, M. W. Urban, D. Rosario, W. Aquino, and J. F. Greenleaf, "Measurement of biaxial mechanical properties of soft tubes and arteries using piezoelectric elements and sonometry," Phys. Med. Biol., vol. 56, p. 3371, 2011, which is incorporated herein by reference in its entirety.

Such models may use various approaches to calculate the moduli based on assumptions of isotropy of the cylinder, transverse isotropy of the cylinder, or transverse isotropy of the cylinder. These models may include a plurality of different constitutive models, a fitted model, curve fitting modeling, of a combination thereof. The stresses and strains in the circumferential directions may be calculated using the expressions for a thin walled cylinder. The stress may be calculated from the measured or applied pressure. The ultrasound and pressure measurements may be synchronized during the acquisition so that the stress-strain curves may be calculated.

In one non-limiting example, a ratio of a mean composite esophageal thickness (2.5 mm) to the radius (7.3 mm) was 0.34, and in the isolated layers was 0.13, as measured in the initial pre-stress state with a pressure of approximately 5 mmHg. Strain and stress measurements may be calculated using different models. The results of the calculations from the various models may be compared in order to evaluate whether an isotropic or anisotropic model may be more appropriate. The stress may be calculated from the pressure. The ultrasound and pressure measurements may be synchronized during the acquisition so that the stress-strain curves may be calculated.

The stresses and strains may be given as:

$$\sigma_L = \frac{Pr}{2h}; \tag{3}$$

$$\sigma_C = \frac{Pr}{h}; \tag{4}$$

$$r = r_{out} - h/2; \tag{5}$$

$$\varepsilon_L = \frac{L - L_0}{L_0}; \tag{6}$$

$$\varepsilon_C = \frac{r - r_0}{r_0}; \tag{7}$$

where σ is the stress, r is the radius, $r_{out}$ is the outer radius, h is the wall thickness, subscripts L and C represent the longitudinal and circumferential directions and the subscript 0 indicates the initial dimension.

In the case where it is assumed that the biological tube is transversely isotropic then:

$$E_C = \frac{3}{4}\frac{\sigma_C}{\varepsilon_C}; \tag{8}$$

$$E_L = \frac{\sigma_C}{2\varepsilon_L + \frac{4}{3}\varepsilon_C}. \tag{9}$$

Alternatively, if the biological tube is assumed isotropic, then:

$$E_{I,1} = \frac{3}{2}\frac{\sigma_c}{(\varepsilon_l + 2\varepsilon_c)}; \tag{10}$$

$$E_{I,2} = \frac{3}{2}\frac{\sigma_l}{(2\varepsilon_l + \varepsilon_c)}; \tag{11}$$

where $E_{I,1}$ and $E_{I,2}$ are the two equivalent relationships of the circumferential and longitudinal characterization of the biological tube tissue isotropically. If the two are not equivalent orthogonally, the equivalency may no longer hold and the tissue may be considered anisotropic. Using the measured stresses and strains, any constitutive model may be used, such as linear or nonlinear models, for example.

In addition to examining thin-walled tubes, the above-described application can also be adapted for thick-walled tubes. To do so, the stress was calculated from the pressure of the esophagus and the different layers were considered as thick-walled tubes. All of the ultrasound and pressure measurements were synchronized during the acquisition so that the stress-strain curves could be calculated as follows:

$$\sigma_L = \frac{P_i r_{i,l}^2 - P_o r_{o,l}^2}{r_{o,l}^2 - r_{i,l}^2}; \tag{12}$$

$$\sigma_C = \frac{P_i r_{i,l}^2 - P_o r_{o,l}^2}{r_{o,l}^2 - r_{i,l}^2} - \frac{r_{o,l}^2 r_{i,l}^2 (P_o - P_i)}{r_l (r_{o,l}^2 - r_{i,l}^2)}; \tag{13}$$

$$h = r_o - r_i; \tag{14}$$

$$\varepsilon_L = \frac{L - L_0}{L_0}; \tag{15}$$

$$\varepsilon_C = \frac{r_{o,l} - r_{o,n}}{r_{o,n}}; \tag{16}$$

where $\sigma$ is the stress, r is the radius, $r_{o,l}$ is the outer radius during loading, $r_{i,l}$ is the inner radius during loading, $r_{o,n}$ is the outer radius at rest, $P_i$ is the pressure in the esophagus, $P_o$ is the pressure outside the esophagus (which can be assumed to be 0, but would need to be determined in different experimental settings), h is the wall thickness, subscripts L and C represent the longitudinal and circumferential directions.

In addition, a strain energy function (SEF) can be used to characterize the mechanical response to applied stress. To use the SEF in this application, its formulation is presented where in the unloaded state the radius is derived from the diameter ($D_{o,n}$):

$$r_{o,n} = D_{o,n}/2 \tag{17}$$

The annular area of the esophagus can be assumed to be constant and incompressible so the inner radius can be calculated from measurements of the outer radius is:

$$A_n = \pi r_{o,n}^2 - \pi r_{i,n}^2 \tag{18}$$

$$h_l = r_{o,l} - \sqrt{r_{o,l}^2 - A_n/\pi} \tag{19}$$

Using these geometric relationships, the longitudinal stretch ratio, $\lambda_{zz}$, is given by:

$$r_{i,l} = \sqrt{r_{o,l}^2 - \frac{A_n}{\pi \lambda_{zz}}}; \tag{20}$$

$$\lambda_{zz} = \frac{A_n}{\pi(r_{o,l}^2 - r_{i,l}^2)}. \tag{21}$$

The longitudinal Green's strain is $$E_{zz} = \frac{\lambda_{zz}^2 - 1}{2}. \tag{22}$$

The circumferential stretch ratio, $\lambda_{\theta\theta}$, and the circumferential Green's strain, $E_{\theta\theta}$, are:

$$\lambda_{\theta\theta} = \frac{r_{i,l} + r_{o,l}}{r_{i,n} + r_{o,n}}; \tag{23}$$

$$E_{\theta\theta} = \frac{\lambda_{\theta\theta}^2 - 1}{2}. \tag{24}$$

The circumferential Kirchoff's stress is:

$$S_{\theta\theta} = \frac{\Delta P r_{i,l}}{h_l \lambda_{\theta\theta}^2}; \tag{25}$$

where $\Delta P$ is the change in pressure between a loaded and unloaded state.

The longitudinal Kirchoff's stress is:

$$S_{zz} = \frac{\pi P r_{i,l}^2}{\lambda_{zz}^2 \pi (r_{o,l}^2 - r_{i,l}^2)}; \tag{26}$$

where $P = P_i$.

Assuming that there is no shear strain, the strain-energy function is given as:

$$\rho_0 W = \frac{C}{2} \exp(Q); \tag{27}$$

$$Q = a_{11}(E_{\theta\theta}^2 - E_{\theta\theta}^{*2}) + a_{22}(E_{zz}^2 - E_{zz}^{*2}) + 2a_{12}(E_{\theta\theta}E_{zz} - E_{\theta\theta}^* E_{zz}^*); \tag{28}$$

where $\rho_0$ is the density of the wall, W is the strain energy per unit mass, C, $a_{11}$, $a_{22}$, and $a_{12}$ are material constants and $E^*_{\theta\theta}$ and $E^*_{zz}$ are strains associated with arbitrarily selected stresses $S^*_{\theta\theta}$ and $S^*_{zz}$, which in this work is associated with the start of the data acquisition. The stresses are given as:

$$S_{\theta\theta} = \frac{\partial(\rho_0 W)}{\partial E_{\theta\theta}} C \exp(Q)(a_{11}E_{\theta\theta} + a_{12}E_{zz}); \tag{29}$$

$$S_{zz} = \frac{\partial(\rho_0 W)}{\partial E_{zz}} C \exp(Q)(a_{22}E_{zz} + a_{12}E_{\theta\theta}). \tag{30}$$

Using the chain rule for the exponential function, the stress equations can be explicitly simplified as:

$$\frac{\partial (\rho_0 W)}{\partial E_{\theta\theta}} = \frac{C}{2}\exp(Q)\frac{\partial Q}{\partial E_{\theta\theta}}; \tag{31}$$

$$\frac{\partial (\rho_0 W)}{\partial E_{zz}} = \frac{C}{2}\exp(Q)\frac{\partial Q}{\partial E_{zz}}; \tag{32}$$

$$S_{\theta\theta} = \frac{C^2}{2}\exp^2(Q)(a_{11}E_{\theta\theta} + a_{12}E_{zz})(2a_{11}E_{\theta\theta} + 2a_{12}E_{zz}); \tag{33}$$

$$S_{zz} = \frac{C^2}{2}\exp^2(Q)(a_{22}E_{zz} + a_{12}E_{\theta\theta})(2a_{22}E_{zz} + 2a_{12}E_{\theta\theta}); \tag{34}$$

where:

$$\frac{\partial Q}{\partial E_{\theta\theta}} = 2a_{11}E_{\theta\theta} + 2a_{12}E_{zz}; \tag{35}$$

$$\frac{\partial Q}{\partial E_{zz}} = 2a_{22}E_{zz} + 2a_{12}E_{\theta\theta}. \tag{36}$$

Fitting of the strain energy functions was performed in MATLAB (MathWorks, Natick, Mass.) with the lsqcurvefit function with specified lower and upper bounds for the parameters C, $\alpha_{11}$, $\alpha_{22}$, and $\alpha_{12}$. The root-mean-square (rms) error was computed between the data and fits for $S_{\theta\theta}$ and $S_{zz}$.

Fitting of the measured strains and pressures could be performed through different modeling approaches with theory for thin wall and thick wall tubes, with different constitutive equations, strain energy functions, curve fitting, or other modeling approaches as appropriate for the application at hand. The processors 213, 325, described above, may also be configured to select at least one of a model for a thick walled tubular structure and a model for a thin walled tubular structure, as appropriate for the application at hand.

The coordinates for the piezoelectric elements in FIG. 1 are given in Table 1.

TABLE 1

Coordinates for crystals in FIG. 1.

| Piezoelectric Element | Coordinates |
|---|---|
| $T_1$ (111) | (0, 0, 0) |
| $T_2$ (121) | ($D_2/2$, $D_2/2$, L) |
| $R_{1,1}$ (113) | ($D_1$, 0, 0) |
| $R_{2,2}$ (115) | ($D_1/2$, $D_1/2$, 0) |
| $R_{1,2}$ (123) | (0, 0, L) |
| $R_{2,1}$ (125) | ($D_2/2$, $-D_2/2$, L) |

The distances between the piezoelectric elements placed at ($x_1$, $y_1$, $z_1$) and ($x_2$, $y_2$, $z_2$) may be computed using:

$$d_{1,2} = \sqrt{(x_1-x_2)^2 + (y_1-y_2)^2 + (z_1-z_2)^2} \tag{37}$$

Based on the example configuration provided in FIG. 1, the distances between different transmitting and receiving piezoelectric elements may be defined and computed in Table 2 where $D_1$ and $D_2$ are the diameters at levels 1 and 2 and L is the length between the two levels.

TABLE 2

Distances between transmitting and receiving crystals in FIG. 1.

| Identifier | Transmitter | Receiver | Distance |
|---|---|---|---|
| $d_{a,1}$ | $T_1$ (111) | $R_{1,1}$ (113) | $D_1$ |
| $d_{b,1}$ | $T_1$ (111) | $R_{2,2}$ (115) | $\sqrt{2}D_1$ |
| $d_{c,1}$ | $T_1$ (111) | $R_{1,2}$ (123) | L |
| $d_{d,1}$ | $T_1$ (111) | $R_{2,1}$ (125) | $\sqrt{D_2^2/2 + L^2}$ |
| $d_{a,2}$ | $T_2$ (121) | $R_{1,1}$ (113) | $\sqrt{D_2^2/4 + (D_1-D_2/2)^2 + L^2}$ |
| $d_{b,2}$ | $T_2$ (121) | $R_{2,2}$ (115) | $\sqrt{2(D_1/2-D_2/2)^2 + L^2}$ |
| $d_{c,2}$ | $T_2$ (121) | $R_{1,2}$ (123) | $\sqrt{2}D_2$ |
| $d_{d,2}$ | $T_2$ (121) | $R_{2,1}$ (125) | $D_2$ |

The example unit array 103 provided in FIG. 1, as illustrated with six piezoelectric elements (two transmitting piezoelectric elements 111 121 and four receiving piezoelectric elements 113, 115, 123, 125) may be repeated in a number of arrays to measure peristalsis or other motions along the length of a section of the esophagus or GI tract, for example, or any biological tube.

Figure 4:
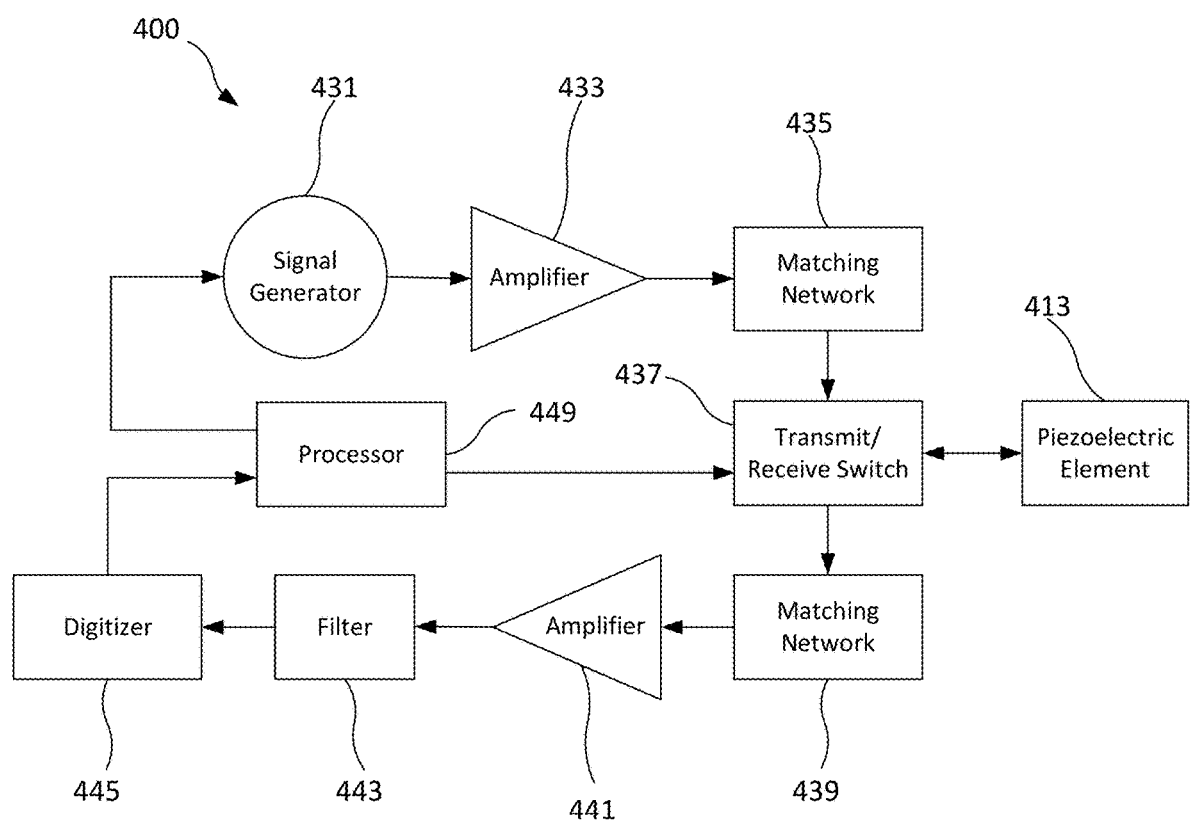
FIG. 4 is a block diagram of example signal transmission and receiving chains connected to a piezoelectric element with a T/R switch in accordance with the present disclosure.

Additionally, as illustrated in FIG. 4, the transmitting and receiving circuits may be coupled to a switchable circuit 400 that controls operation of a piezoelectric element 413 that can then switch between transmit and receive functions. For example, a signal generator 431 is coupled to an amplifier 433 and matching network 435 to form a transmission circuit. The transmission circuit is coupled through a transmit/receive switch 437 to a receive circuit that may include a matching network 439, amplifier 441, filter 443, and digitizer 445. In operation, a processor 449 may control operation of the transmit/receive switch 437 to couple the piezoelectric element 413 to the transmit circuit 431, 433, 435 or the receive circuit 439, 441, 443, 445 and receive feedback to provide analysis and reports. Thus, FIG. 4 illustrates how the transmit and receive signal chains from FIGS. 1 and 2, respectively, can be coupled to a common piezoelectric element 413 to create a switchable network.

The above-described systems and methods can be used in a variety of applications, including GI, vascular, and other clinical analysis processes. The following provides non-limiting examples of but a few applications of the above-described systems and methods.

EXAMPLES

The aim of these experiments was to investigate biomechanical properties of esophageal tissues through nondestructive testing utilizing sonometry in ex vivo esophageal tissues. The esophagus represents a useful target for tissue engineering strategies based on relative simplicity in comparison to other organs. Malignant esophageal pathologies typically require resection of the esophagus and reconstruction to restore foregut continuity. Reconstruction options are limited and morbid. Current methods for mechanical testing of esophageal tissues both in vivo and ex vivo are either destructive or ignore anisotropy.

The structure of the esophagus underlies its function of propulsion of food into the stomach. It performs this function through organized peristalsis as a result of synchronization of the neuromuscular components. Importantly, this function necessitates mechanical tolerances of the esophagus that are able to withstand repetitive mechanical stress and strains of passage of oral bolus down the gastro intestinal tract; the esophagus must expand from the resting collapsed state to a dilated state to accommodate oral bolus repetitively without rupture or leak. Understanding the biomechanical relationship and varied contributions of the mucosal-submucosal component and the muscular component to composite biomechanical effects is required to elucidate dysmotility syndromes as well for future work to generate suitable constructs for tissue engineered approaches to the esophagus which require resection and replacement of esophageal pathologies such as malignancy.

The impact of esophageal cancer is severe, with dismal outcomes. Esophageal cancer affects approximately a half million new people worldwide annually, and is increasing in the United States. Surgical management requires esophageal resection and subsequent reconstruction. Currently reconstruction of the native esophagus is impossible given the limited redundancy of tissue and poor vascularization. Therefore, reconstruction typically utilizes autologous tissue, either gastric, small bowel, or colon as a conduit with removal of the esophagus distal to the diseased segment. These treatment modalities have been associated with high morbidity and mortality. Given these limitations in treatment, there is a critical need for a tissue engineered substitute. An esophageal substitute would ideally recapitulate the mechanical properties of the native esophagus. Generated esophageal constructs would ideally be mechanically assessed in a non-destructive method to determine suitability and fitness for implantation.

The composite structure of the esophagus represents a unique opportunity for both mechanical testing and tissue engineering as compared to other tubular structures of the body. There is an easily detached interface between the esophageal mucosa-submucosa and the muscular layers. These separate layers reflect different nonlinear material properties, but the degree of anisotropy remains unclear.

In this experiment a previous theory was applied for the characterization of arteries and their nonlinear mechanical response and approximate degree of anisotropy to the composite, mucosal-submucosal and muscular layers independently to determine biaxial stress strain and approximate anisotropy within the composite and separate layers of the esophagus.

The methods and systems used in this experiment allow for biomechanical determination of tissue properties, particularly longitudinal and circumferential moduli. The relative contribution of mucosal-submucosal layers and muscular layers were compared to composite esophagi. Swine thoracic esophageal tissues (n=5) were tested. For example, as will be described with respect to FIG. 5A, stress was generated using pressure loading created by a continuous pressure pump system 563, which operated as the pressure device. Preconditioning of tissue was performed by pressure loading with the pump system 563 before data was recorded. Sonometry using piezocrystals, such as using the above-described systems and methods, was utilized to determine longitudinal and circumferential strain on composite esophagi. Similarly, five mucosa-submucosal and five muscular layers from thoracic esophagi were tested independently.

The experimental results for esophageal tissues using this measurement method were consistent with reported uniaxial and biaxial mechanical testing. However, this measurement method provides a non-destructive means to assess biomechanical properties. This method may be of use to characterize mechanical properties of tissue engineered esophageal constructs.

Thus, a nondestructive method for mechanical assessment was applied using piezoelectric elements and sonometry, such as described above, to determine biaxial mechanical properties in ex vivo esophagi. To characterize the isotropic and anisotropic properties of esophageal tissue, multiple esophageal muscle and mucosal-submucosal layer samples, and composite esophagi were tested. Biomechanical characterizations were performed with pressure loading and measurements of the radial and longitudinal strain made using piezocrystal sonometry. From the applied pressure and measured strain values, the circumferential and longitudinal moduli were computed under assumptions of anisotropic and isotropic structure.

Fifteen esophagi were harvested from 60-70 kg domestic swine euthanized according to Institutional Animal Care Use Committee guidelines. The entire esophagus: cervical, thoracic and abdominal portions were mobilized and excised through either a median sternotomy, or right thoracotomy. The fresh tissue was stored in phosphate buffered saline (NaCl 137 mmol/L KCL 2.7 mmol/L $Na_2HPO_4$ 10 mmol/L $KH_2PO_4$ 1.8 mmol/L) until transfer to −80° C. freezer. Esophageal specimens were gently mechanically separated to generate samples (composite n=5, mucosa-submucosa n=5, and muscular n=5 layers) used for testing. Small piezoelectric elements (Sonometrics, London, Ontario, Canada) were then affixed to the outer wall of the specimen using 8-0 suture, as fully described below and shown in FIG. 5. The specimen was then trimmed so 12 cm of mid-thoracic esophagus was isolated, which was then mounted on cannulae and fixed with plastic securement ties so that 10 cm of esophageal tissue was exposed. After cannulation, each segment was filled with degassed normal saline until free of air at a baseline pressure of ~5 mmHg and immersed vertically in a bath of normal saline 565 and mounted on a holding frame 561. One end of the esophagus was tied off and a weight 551 was attached to give a small pre-stress to an in vivo length. The experimental setup is shown in FIG. 5.

Figure 5A:
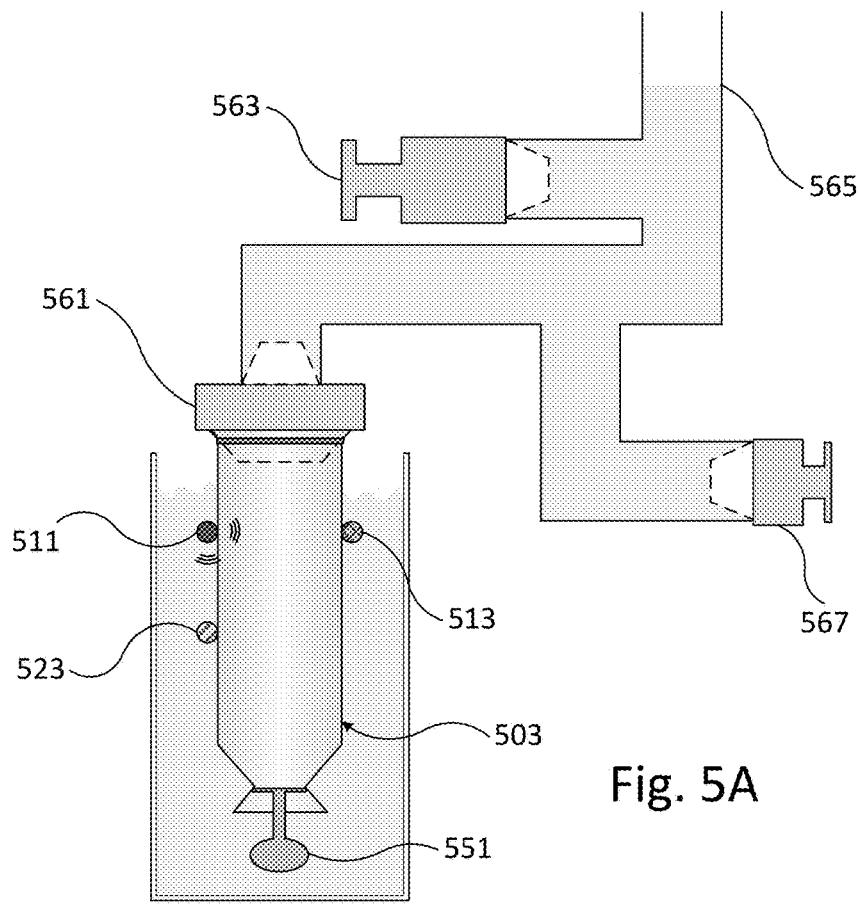
FIG. 5A is an illustration of an experimental setup for sonometric esophageal testing in accordance with the present disclosure.

As seen in FIG. 5A, the esophagus 503 was submerged in degassed saline and pre-strained to an in vivo length. The sonometric and pressure transducer signal processing chain is also shown alongside the experimental setup in FIG. 5B to create a fuller overview of the systems and methods employed.

A proximal esophageal cannula was attached to a calibrated pressure transducer 567 that was downstream along the saline 565 from the continuous pressure pump system 563. Deformation of the esophagus 503 under a time-varying pressure load (KDS210, Kd Scientific, Holliston, Mass.) and measured (PX319-015G5V, Omegadyne Inc., Sunbury, Ohio) and unloading sequence generated biaxial strain with observed hysteresis, allowing the circumferential and longitudinal moduli $E_C$ and $E_L$, respectively, to be determined. This method was applied to ex vivo native esophagi with (n=5) loading and unloading cycles for preconditioning. Infusion and withdrawal of 15 mL was performed at a volume at 60 mL/min. The speed of sound in the saline 565 was assumed to be 1480 m/s and the time of flight was calculated from distances which were measured between the elements with calipers.

In this non-limiting example, a piezoelectric element 511 was designated for transmission only and two other piezoelectric elements 513, 523 were used as receivers. One of the receiving piezoelectric elements 513 was placed at the same level as the transmitting piezoelectric element 511 but across the diameter of the esophagus 503, and the other piezoelectric element 523 was placed along the length of the esophagus 503 on the same side as the transmitting piezoelectric element 511 about 2 cm away.

Figure 5B:
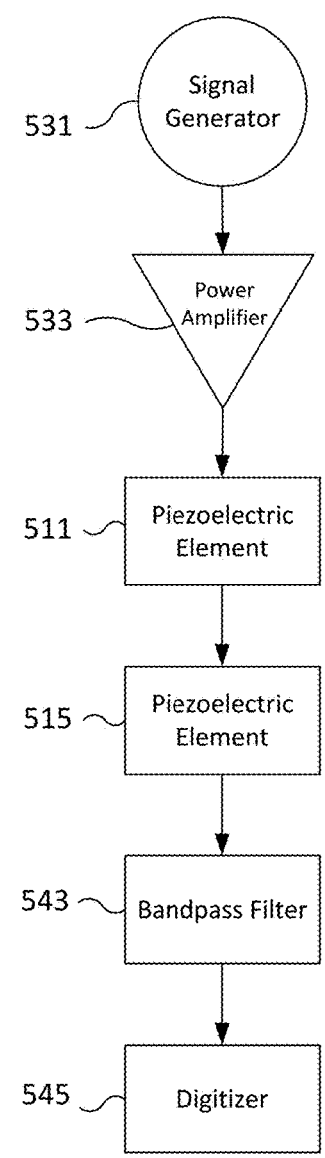
FIG. 5B is a block diagram of the electronics for the experimental setup of FIG. 5A.

As illustrated in the block diagram of FIG. 5B, a signal generator 531 (33120, Agilent, Palo Alto, Calif.) was used to create a ten-cycle burst at 2 MHz (5 μs) with a pulse repetition frequency of 20 Hz. The signal was amplified by a custom-made 40 dB power amplifier 533. The received signals on each of the receiving piezoelectric elements 513, 523, 515 were amplified with custom-made amplifiers and filtered with 2 MHz bandpass filters 543. These signals were digitized at 100 MHz by a digitizer 545 (ATS460, Alazartech, Montreal, QC, Canada). The total length of time for the measurements was 60 seconds.

Referring again to FIG. 5B, in this example, the piezoelectric elements 511, 513, 523 were coupled directly to the esophagus 503. However, as described above, the piezoelectric elements 511, 513, 523 can be mounted on a substrate that is configured to engage the esophagus 503 or other tubular biological structure. That is the piezoelectric elements 511, 513, 523 may be mounted on a tubular substrate that is designed to wrap around or fit as a sleeve around the esophagus 503. However, in this example, the piezoelectric elements 511, 513, 523 were mounted to the esophagus so that multiple measurements cycles could be performed while monitoring the relative placement of the piezoelectric elements 511, 513, 523 about particular positions of the esophagus 503. Five preconditioning cycles were performed for each sample in order to obtain consistent results, but the degree of preconditioning which occurred may vary based on the sample.

FIG. 6 shows a series of correlated graphs of the measured displacements and pressures, as well as the calculated stress, strains, and moduli for the anisotropic characterization of a composite sample assuming a thin walled tube geometry. The five curves are from consecutive measurements. As can be seen from the graphs, the agreement in the data is very good between acquisitions.

Figure 6A:
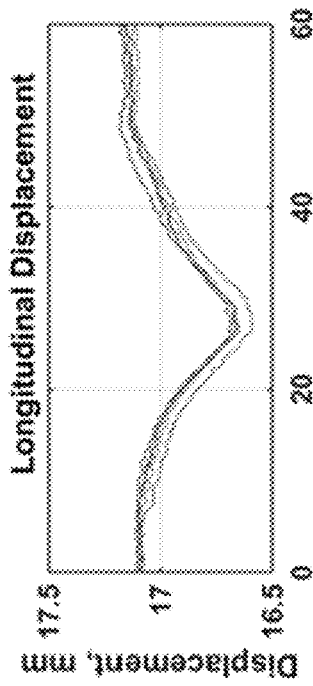
FIG. 6A is a graph showing circumferential displacement measured using an example of a composite sample in accordance with the present disclosure.
Figure 6C:
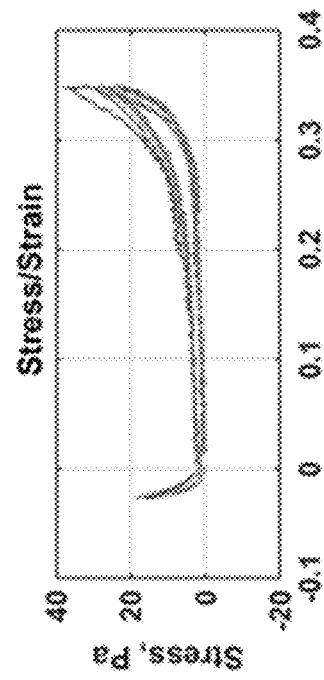
FIG. 6C is a graph showing pressure measured using an example of a composite sample in accordance with the present disclosure.
Figure 6E:
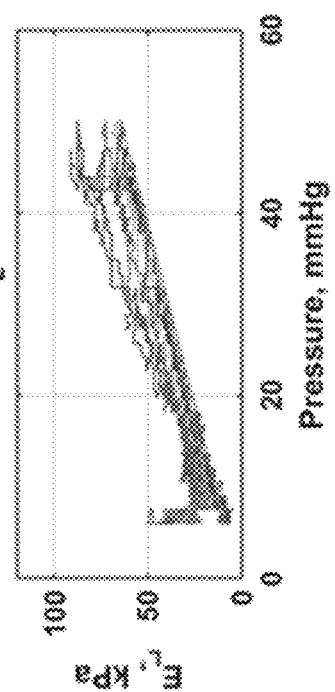
FIG. 6E is a graph showing $E_c$ measured using an example of a composite sample in accordance with the present disclosure.
Figure 6B:
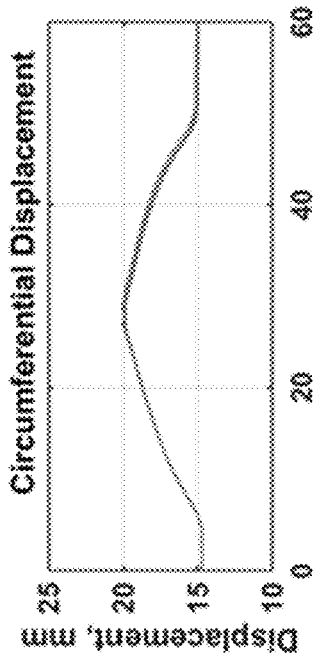
FIG. 6B is a graph showing longitudinal displacement measured using an example of a composite sample in accordance with the present disclosure.
Figure 6D:
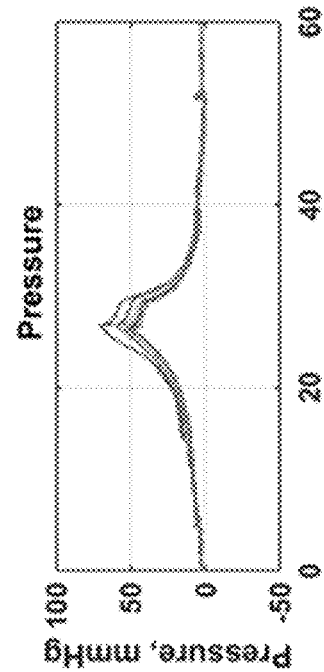
FIG. 6D is a graph showing stress/strain measured using an example of a composite sample in accordance with the present disclosure.
Figure 6F:
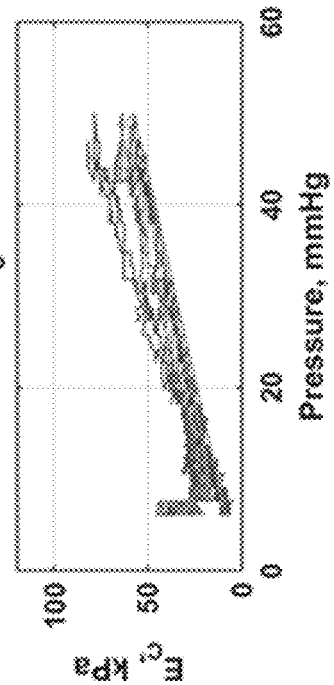
FIG. 6F is a graph showing $E_L$ measured using an example of a composite sample in accordance with the present disclosure.

As seen in FIGS. 6A-6F, a typical example from five repeated measurements from one composite esophageal sample. In particular, FIG. 6A shows the circumferential displacement, FIG. 6B shows the longitudinal displacement, FIG. 6C shows the pressure, FIG. 6D show the stress and strain curves, FIG. 6E show $E_C$, and FIG. 6F shows $E_L$.

Figure 7B:
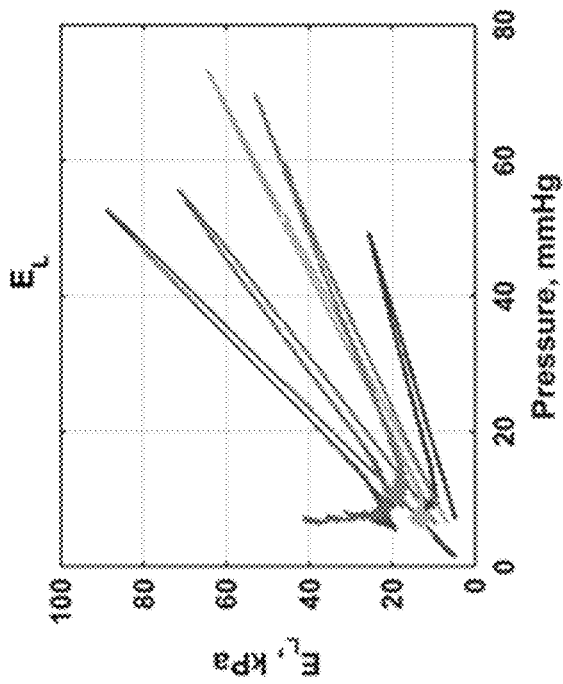
FIG. 7B is a graph showing the results for the anisotropic and isotropic calculations for the five composite samples in accordance with the present disclosure, illustrating $E_L$.
Figure 7D:
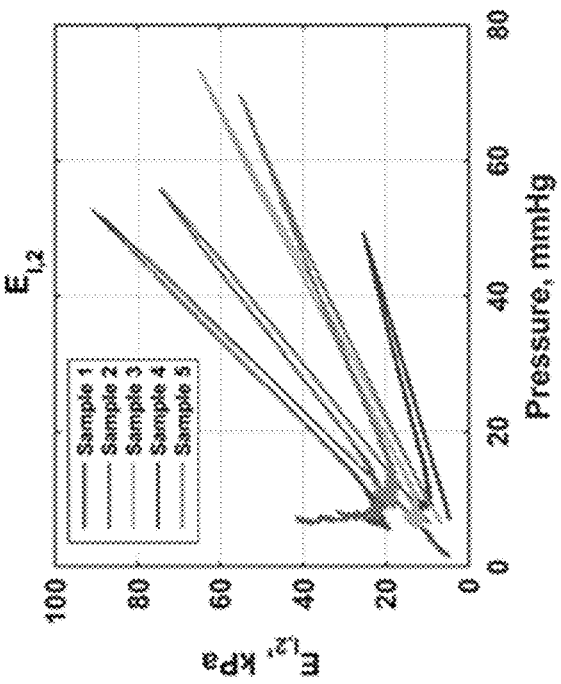
FIG. 7D is a graph showing the results for the anisotropic and isotropic calculations for the five composite samples in accordance with the present disclosure, illustrating $E_{I,2}$.
Figure 7A:
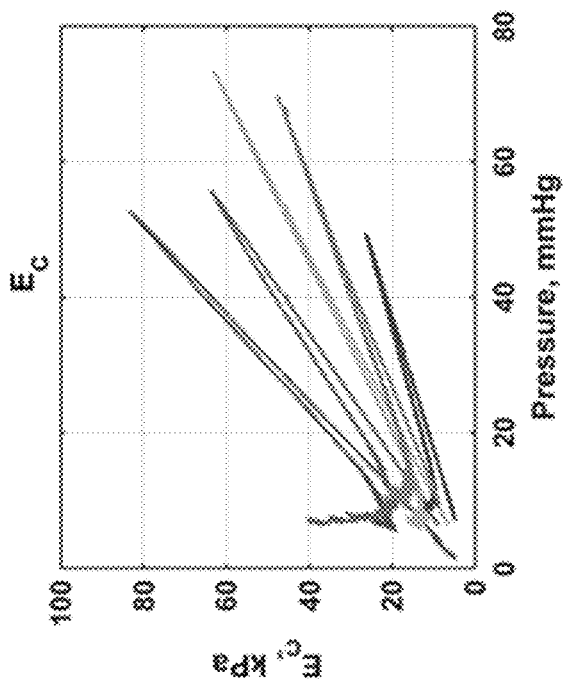
FIG. 7A is a graph showing the results for the anisotropic and isotropic calculations for the five composite samples in accordance with the present disclosure, illustrating $E_C$.
Figure 7C:
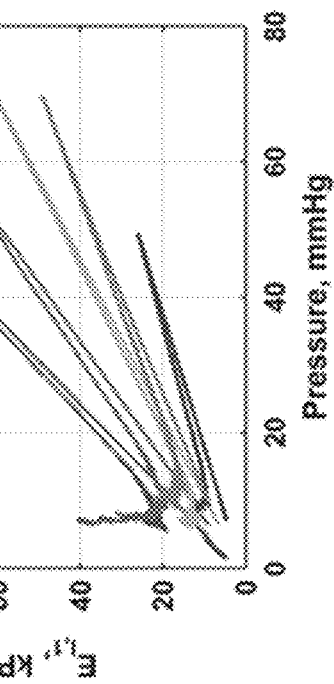
FIG. 7C is a graph showing the results for the anisotropic and isotropic calculations for the five composite samples in accordance with the present disclosure, illustrating $E_{I,1}$.

The correlated graphs in FIGS. 7A-7D show the results for the anisotropic and isotropic calculations for the five composite samples. Each curve is the mean of five repeated acquisitions. In particular, FIGS. 7A-7D show the characterization of the composite esophageal samples. The large asymptotes in the moduli at low pressures are artifacts related to low and noisy strain values that are manifested as large moduli. FIG. 7A shows $E_C$, FIG. 7B shows $E_L$, FIG. 7C shows $E_{I,1}$, and FIG. 7D shows $E_{I,2}$, as labeled.

Using the data in FIGS. 7A-D, the medians and interquartile ranges (IQRs) at each pressure during loading and unloading were computed to evaluate the natural variation between samples for the anisotropic and isotropic characterizations. The results for these calculations are shown in the correlated graphs of FIGS. 8A and 8B. Not all samples were tested at pressures higher than 50 mmHg, therefore data from these pressures were not included in the calculated and plotted of median and IQRs for each elastic modulus. The similarity between $E_C$ and $E_L$ as well as the isotropic characterizations indicated that the composite configuration may be adequately approximated as an isotropic tube.

Figure 8A:
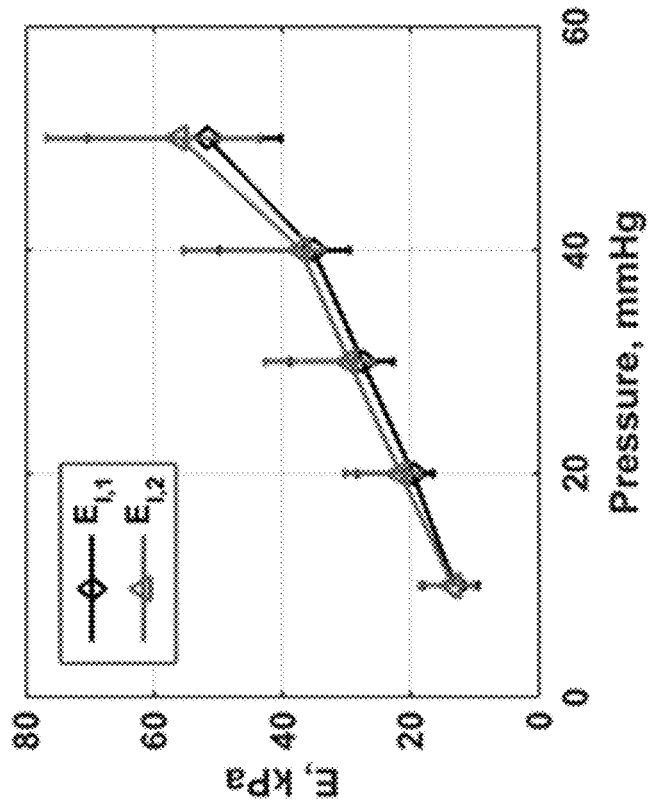
FIG. 8A provides a graph showing a moduli variation versus pressure for the composite esophageal samples using the transverse isotropic model in accordance with the present disclosure.
Figure 8B:
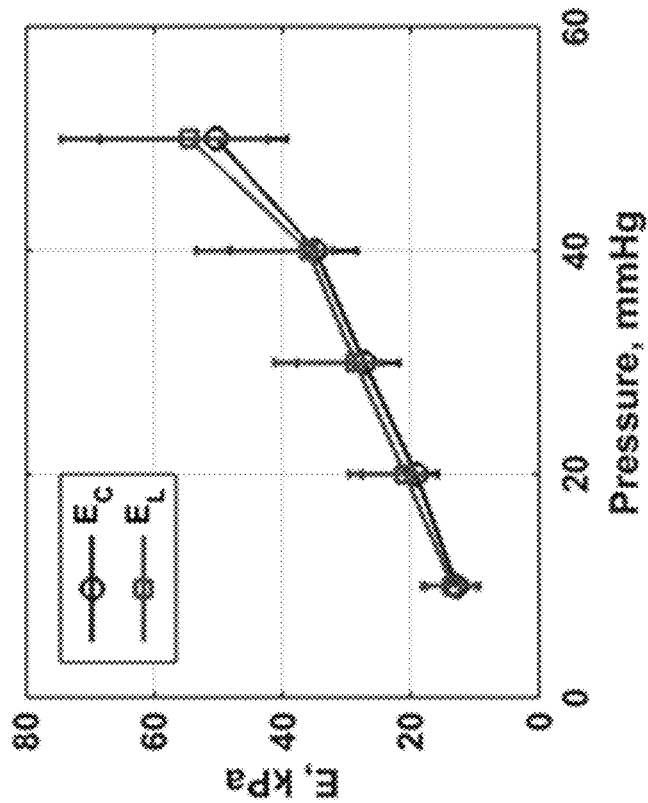
FIG. 8B provides a graph showing a moduli variation versus pressure for the composite esophageal samples using the isotropic model in accordance with the present disclosure.

FIGS. 8A and 8B show the variation of the moduli with pressure. The muscle layer results showed good agreement between the anisotropic and isotropic cases, so an isotropic characterization may be most appropriate. As seen in FIGS. 8A and 8B, the graphs show the summary of moduli variation versus pressure for the composite esophageal samples. Moduli at pressures greater than 50 mmHg are not presented as there were limited samples reaching those pressure values. Specifically, the graphs show the transverse isotropic model (FIG. 8A) and the isotropic model (FIG. 8B). The open symbols are the median and the error bars represent the IQR.

Figure 9A:
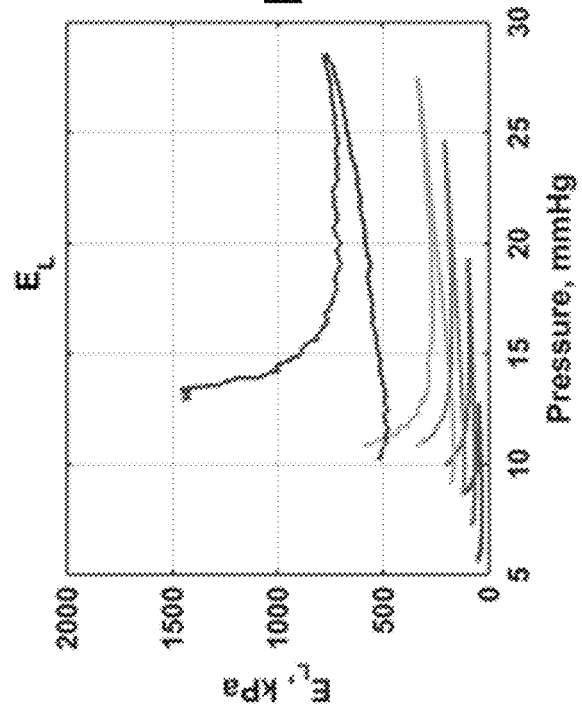
FIG. 9A provides a graph showing the results of the anisotropic and isotropic calculations for the five mucosal layer samples in accordance with the present disclosure, illustrating $E_C$.
Figure 9B:
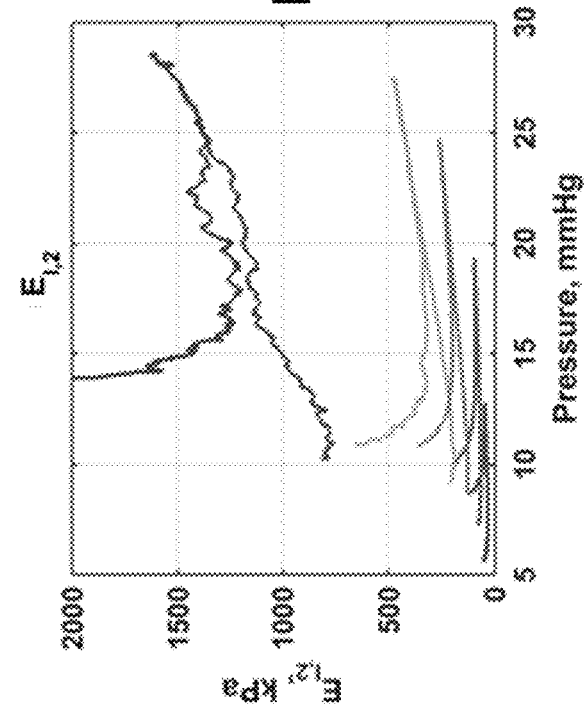
FIG. 9B provides a graph showing the results of the anisotropic and isotropic calculations for the five mucosal layer samples in accordance with the present disclosure, illustrating $E_L$.
Figure 9C:
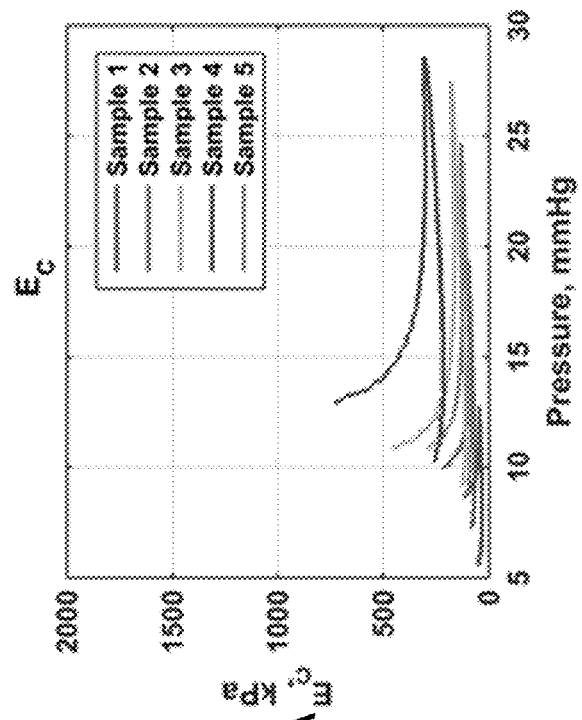
FIG. 9C provides a graph showing the results of the anisotropic and isotropic calculations for the five mucosal layer samples in accordance with the present disclosure, illustrating $E_{I,1}$.
Figure 9D:
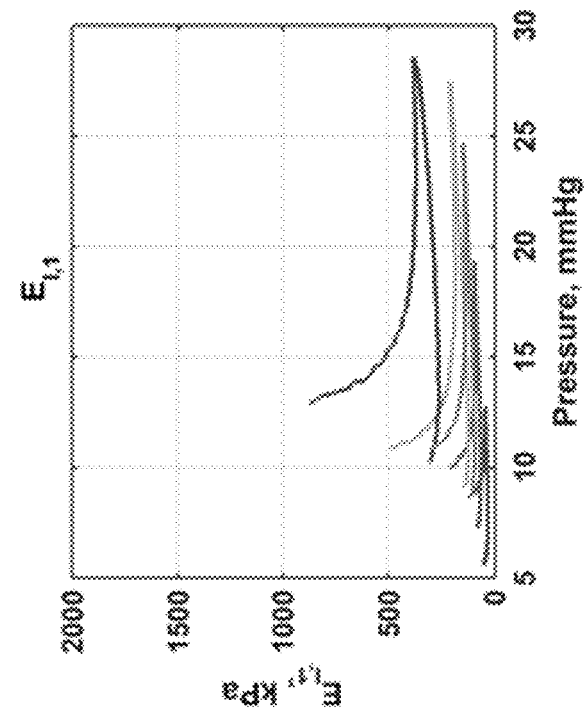
FIG. 9D provides a graph showing the results of the anisotropic and isotropic calculations for the five mucosal layer samples in accordance with the present disclosure, illustrating $E_{I,2}$.

FIGS. 9A-9D provide a series of correlated graphs illustrating the results of the anisotropic and isotropic calculations for the five mucosal layer samples. As in FIGS. 7A-7D, each curve is the mean of five repeated acquisitions. As seen in FIGS. 9A-9D, the characterization of the mucosal layer samples can be seen. FIG. 9A shows $E_C$, FIG. 9B shows $E_L$, FIG. 9C shows $E_{I,1}$, and FIG. 9D shows $E_{I,2}$.

FIGS. 10A and 10B show the variation of the moduli with pressure. In the mucosal layer samples it was found that $E_L$ was always greater than $E_C$ and the isotropic cases did not show good agreement. In this case, an anisotropic characterization of the mucosal layer may be more appropriate. The large asymptotes in the moduli at low pressures are artifacts related to low and noisy strain values that are manifested as large moduli. Moduli at pressures greater than 24 mmHg are not presented as there were limited samples reaching those pressure values. As seen in FIGS. 10A and 10B, the graphs show the summary of moduli variation versus pressure for the mucosal layer samples. The graphs show the transverse isotropic model (FIG. 10A) and the isotropic model (FIG. 10B). The open symbols are the median and the error bars represent the IQR.

Figure 11A:
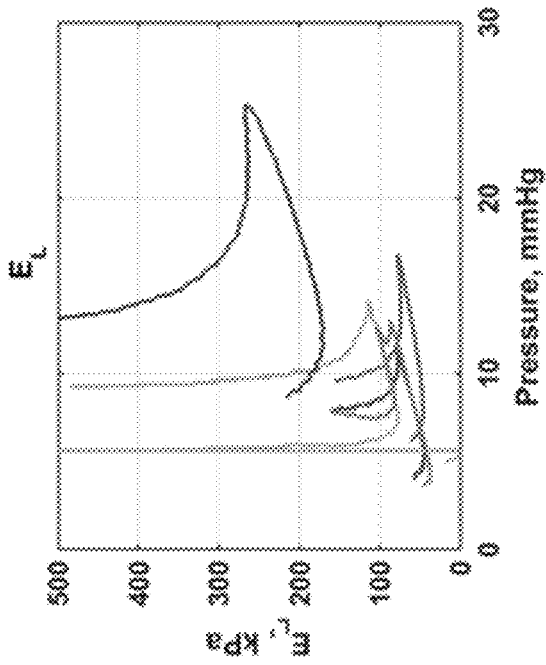
FIG. 11A provides a graph showing the results of the anisotropic and isotropic calculations for the five muscle layer samples and five repeated acquisitions in accordance with the present disclosure, illustrating $E_C$.
Figure 11B:
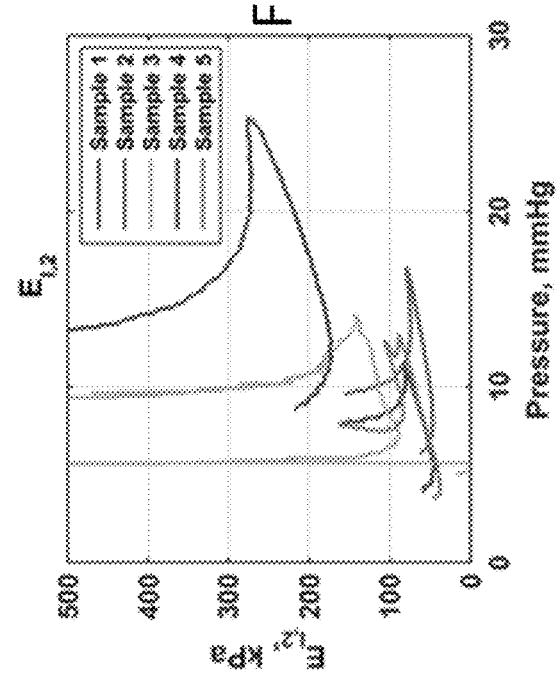
FIG. 11B provides a graph showing the results of the anisotropic and isotropic calculations for the five muscle layer samples and five repeated acquisitions in accordance with the present disclosure, illustrating $E_L$.
Figure 11C:
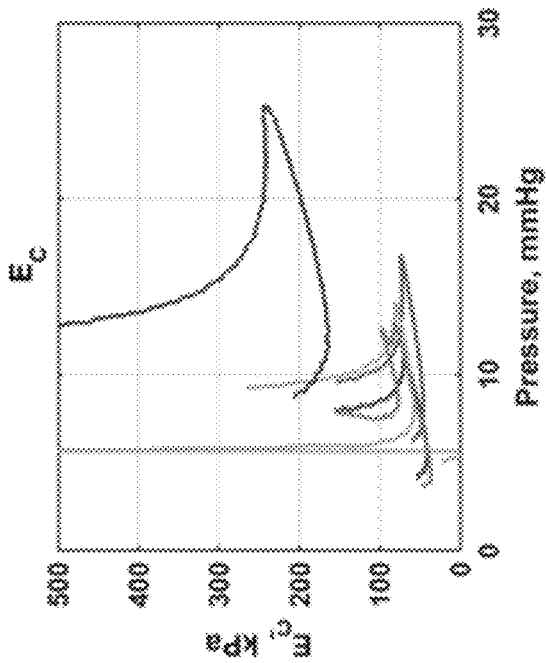
FIG. 11C provides a graph showing the results of the anisotropic and isotropic calculations for the five muscle layer samples and five repeated acquisitions in accordance with the present disclosure, illustrating $E_{I,1}$.
Figure 11D:
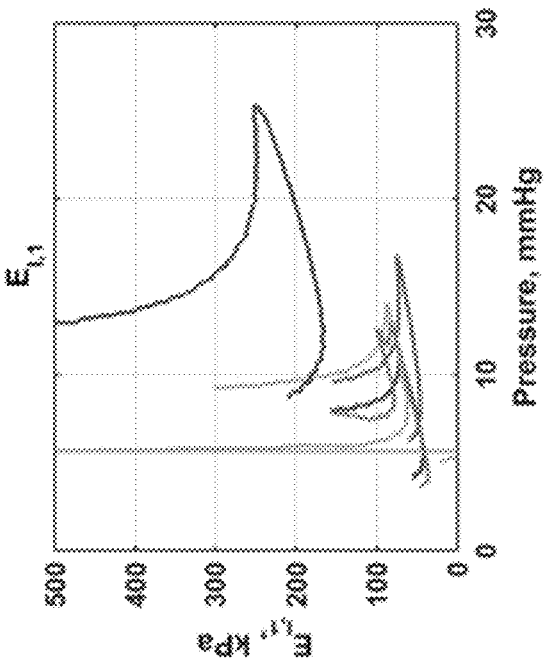
FIG. 11D provides a graph showing the results of the anisotropic and isotropic calculations for the five muscle layer samples and five repeated acquisitions in accordance with the present disclosure, illustrating $E_{I,2}$.

FIGS. 11A-11D show results of the anisotropic and isotropic calculations for the five muscle layer samples and five repeated acquisitions. The large asymptotes in the moduli at low pressures are artifacts related to low and noisy strain values that are manifested as large moduli. The graphs show the characterization of the muscle layer samples. FIG. 11A shows $E_C$, FIG. 11B shows $E_L$, FIG. 11C shows $E_{I,1}$, and FIG. 11D shows $E_{I,2}$.

Figure 12A:
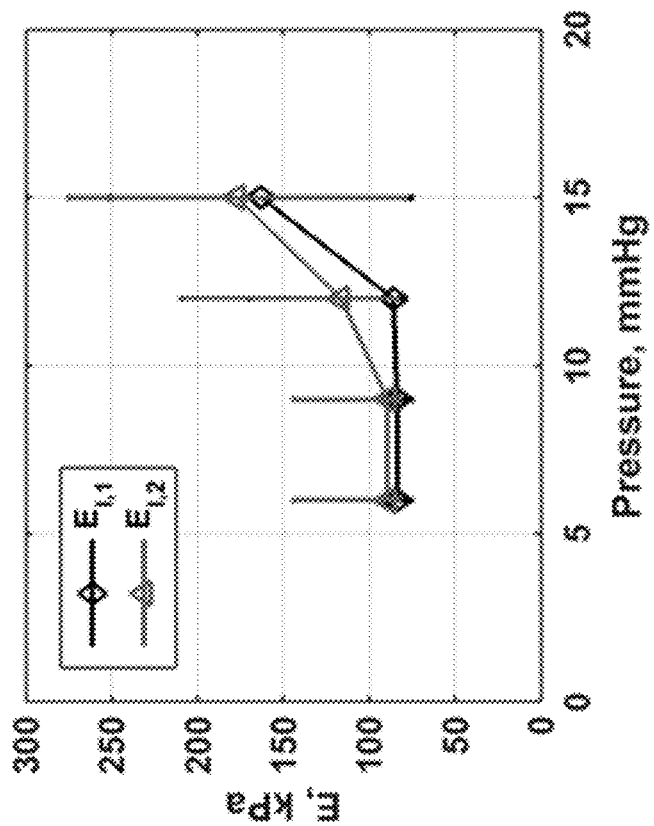
FIG. 12A a graph showing the summary of moduli variation versus pressure for the muscular layer samples using the transverse isotropic model in accordance with the present disclosure.
Figure 12B:
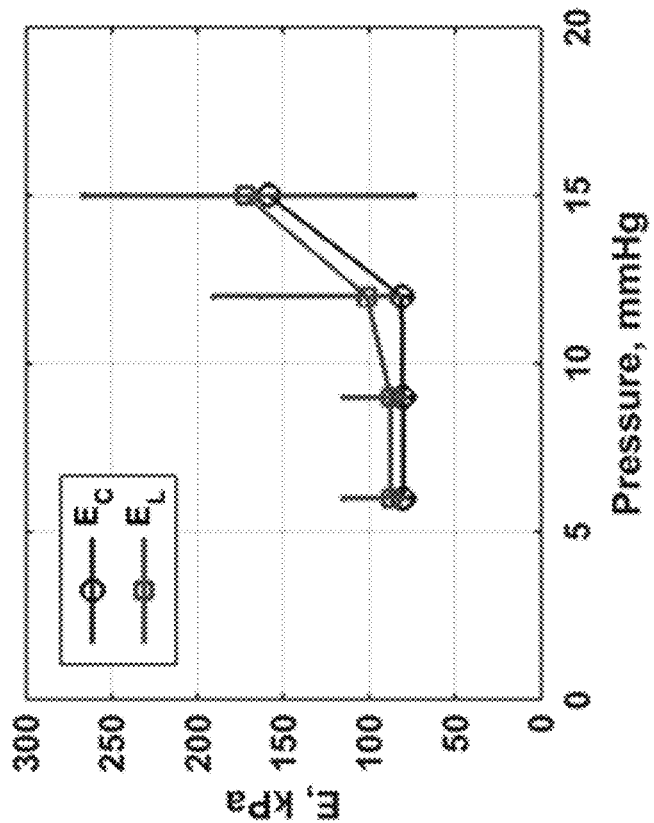
FIG. 12B a graph showing the summary of moduli variation versus pressure for the muscular layer samples using the isotropic model in accordance with the present disclosure.

As seen in FIGS. 12A and 12B, correlated graphs are provided that show the summary of moduli variation versus pressure for the muscular layer samples. Moduli at pressures greater than 15 mmHg are not presented as there were limited samples reaching those pressure values. The graphs show the transverse isotropic model (FIG. 12A), and the isotropic model (FIG. 12B). The open symbols are the median and the error bars represent the IQR.

Using this system, the displacements, longitudinal ($E_L$) and circumferential moduli ($E_C$), and pressure loading in both composite and isolated or separated specimens were able to be reproducibly demonstrated. The mucosa-submucosa $E_C$ ranged from 175-225 kPa, and $E_L$ ranged from 250-550 kPa under pressure range of 6-27 mmHg. The muscular layer $E_C$ ranged from 100-250 kPa, and $E_L$ ranged from 120-245 kPa tested over a pressure range of 6-21 mmHg. The composite esophagi $E_C$ ranged from 15-60 kPa, and $E_L$ ranged from 16-60 kPa over a pressure load of 10-70 mmHg. The data ranges are summarize in Table 3.

TABLE 3

Summary of esophageal testing results.

| Configuration | Pressure Range, mmHg | Maximal Circumferential Strain. Median (IQR) | Maximal Longitudinal Strain. Median (IQR) | $E_C$, kPa | $E_L$, kPa |
|---|---|---|---|---|---|
| Composite | 10-70 | 0.44 (0.38) | −0.029 (0.02) | 15-60 | 16-60 |
| Mucosal Layer | 6-27 | 0.179 (0.075) | −0.031 (0.031) | 175-225 | 250-550 |

TABLE 3-continued

Summary of esophageal testing results.

| Config-uration | Pressure Range, mmHg | Maximal Circumferential Strain. Median (IQR) | Maximal Longitudinal Strain. Median (IQR) | $E_C$, kPa | $E_L$, kPa |
|---|---|---|---|---|---|
| Muscle Layer | 6-21 | 0.167 (0.201) | −0.008 (0.013) | 100-250 | 120-245 |

It was observed that the moduli of the composite samples were much lower than for the individual layers, particularly the mucosal-submucosal layer, which has been previously demonstrated and is reproduced in testing. One could make an analogy that the two layers act as springs in series, and the effective stiffness or modulus is lower than the two individual layers.

Further, from these experiments it was determined that the mucosa and submucosal layers demonstrate anisotropic properties compared to the muscular and composite esophagus which appear to behave isotropically. The only pronounced change between isotropic and anisotropic models in our findings existed in the mucosa-submucosa, which has been shown to exhibit a highly oriented collagen content.

The resulting data supports the use, and reproducibility of piezoelectric elements and sonometry to assess the ex vivo biaxial mechanical properties of the esophagus as a composite structure and mucosa-submucosa and muscular isolated layers. It was observed in this experiment that the composite esophagus and the muscle layer behaved as an isotropic tube, but the mucosa-submucosal layer acted as an anisotropic tube. The application of this technique may be of utility in nondestructive biomechanical assessment of tissue engineered esophagi.

For the thick walled tube assumption the thick wall stress calculations or SEF equations can be used for the mechanical property characterization. In particular, as will be described, FIGS. 13A-17F show examples of the measured displacements and pressures and the calculated stress, strains for a composite, mucosa-submucosa, and muscle sample, respectively. The curves are from consecutive measurements. The agreement is generally very good between acquisitions.

Specifically, FIGS. 13A-13F provide graphs showing typical example data from five repeated measurements from one composite esophageal sample. FIG. 13A shows circumferential displacement. FIG. 13B shows longitudinal displacement. FIG. 13C shows pressure. FIG. 13D shows circumferential stress and strain curves. FIG. 13E shows longitudinal stress and strain curves. FIG. 13F shows circumferential Kirchoff stress and Green's strain.

FIGS. 14A-14F provide graphs showing typical example data from five repeated measurements from one mucosa-submucosa sample. FIG. 14A shows circumferential displacement. FIG. 14B shows longitudinal displacement. FIG. 14C shows pressure. FIG. 14D shows circumferential stress and strain curves. FIG. 14E shows longitudinal stress and strain curves. FIG. 14F shows circumferential Kirchoff stress and Green's strain.

Figure 15A:
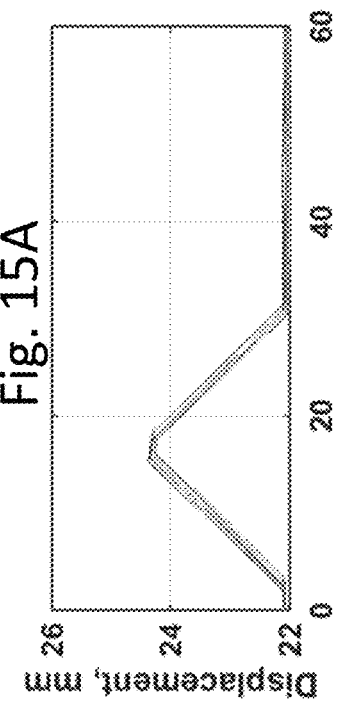
FIG. 15A is a graph showing circumferential displacement measurements from one esophageal muscle sample.
Figure 15B:
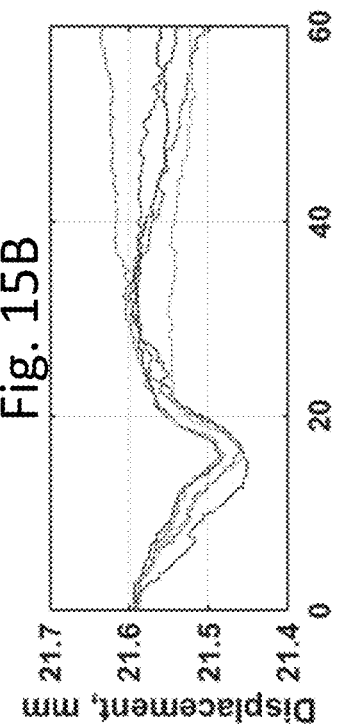
FIG. 15B is a graph showing longitudinal displacement measurements from one esophageal muscle sample.
Figure 15C:
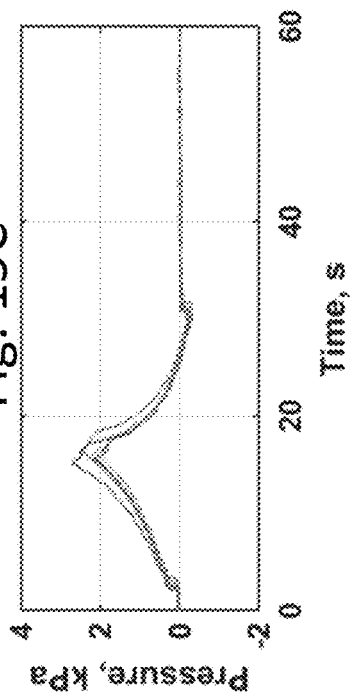
FIG. 15C is a graph showing pressure measurements from one esophageal muscle sample.
Figure 15D:
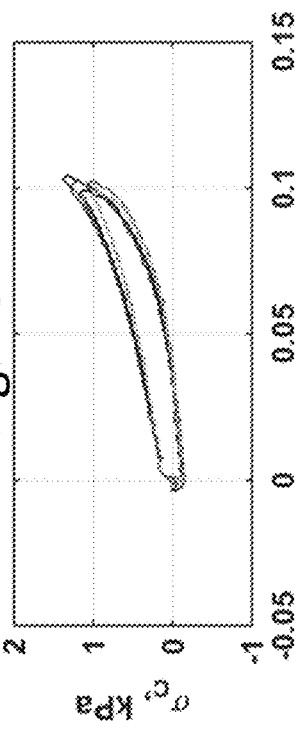
FIG. 15D is a graph showing circumferential stress and strain curves from one esophageal muscle sample.
Figure 15E:
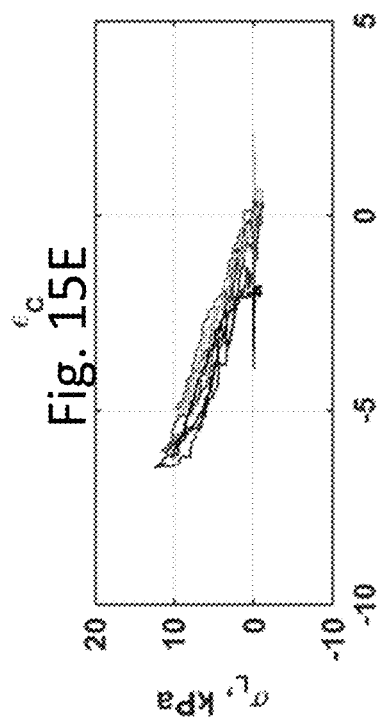
FIG. 15E is a graph showing longitudinal stress and strain curves from one esophageal muscle sample.
Figure 15F:
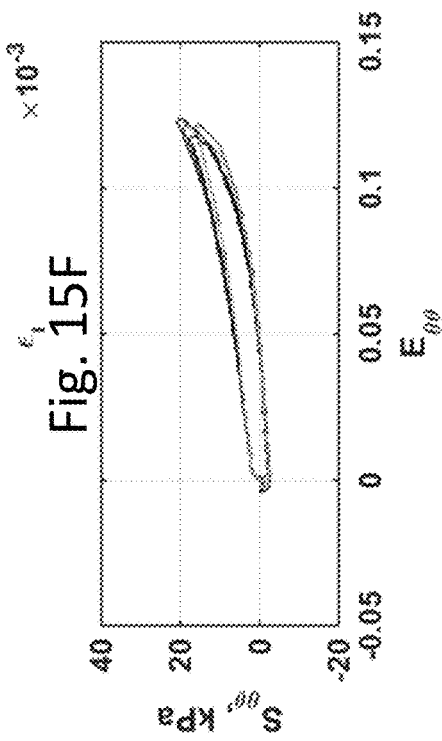
FIG. 15F is a graph showing circumferential Kirchoff stress and Green's strain from one esophageal muscle sample.

FIGS. 15A-15F provide graphs showing a typical example data from five repeated measurements from one esophageal muscle sample. FIG. 15A shows circumferential displacement. FIG. 15B shows longitudinal displacement. FIG. 15C shows pressure. FIG. 15D shows circumferential stress and strain curves. FIG. 15E shows longitudinal stress and strain curves. FIG. 15F shows circumferential Kirchoff stress and Green's strain.

Figure 16A:
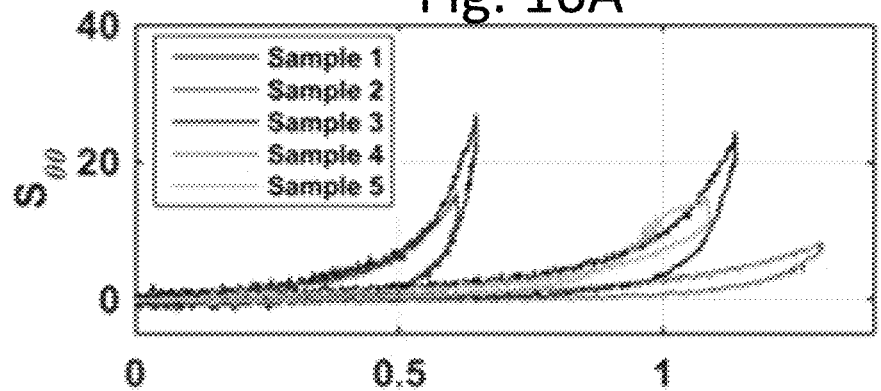
FIG. 16A is a graph showing Kirchoff stress versus Green's strain for composite samples.
Figure 16B:
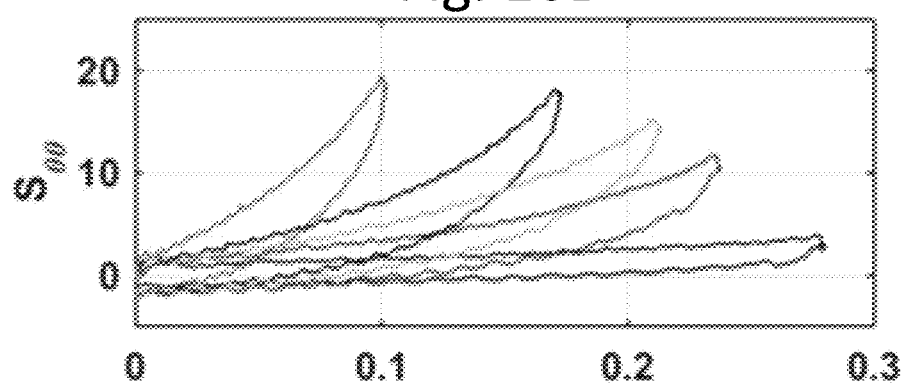
FIG. 16B is a graph showing Kirchoff stress versus Green's strain for mucosa-submucosa samples.
Figure 16C:
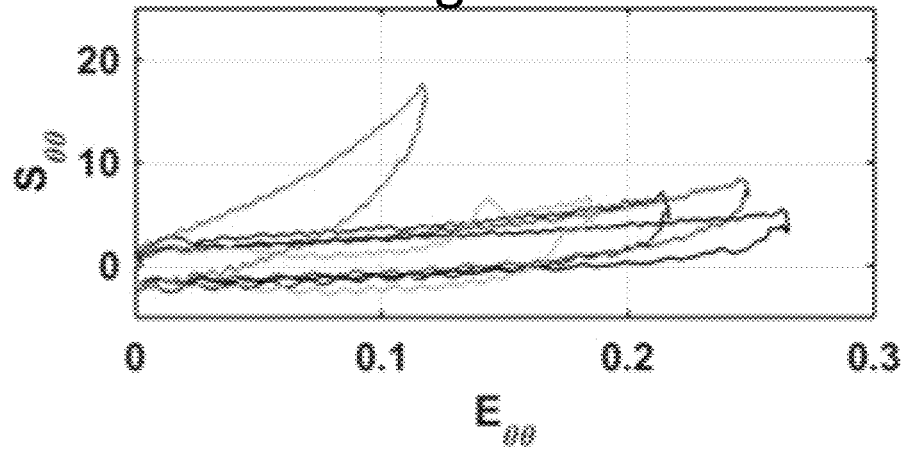
FIG. 16C is a graph showing Kirchoff stress versus Green's strain for mucosa-submucosa samples.

FIGS. 16A-16C provide graphs showing the circumferential Kirchoff stress versus Green's strain from one acquisition for the five samples for each configuration. In particular, FIG. 16A is a graph that shows Kirchoff stress for composite samples. FIG. 16B shows Kirchoff stress for mucosa-submucosa samples. FIG. 16C shows Kirchoff stress for muscle samples.

Figure 17D:
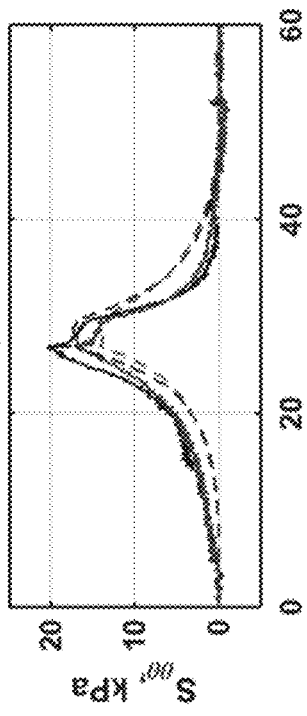
FIG. 17D is a graph showing examples of the SEF fits and the Kirchoff stresses through time for the results shown in FIGS. 13A-16C for two consecutive acquisitions to show themucosa-submucosa, $S_{zz}$.
Figure 17E:
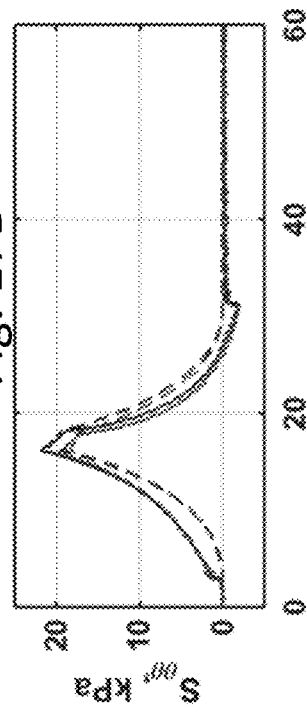
FIG. 17E is a graph showing examples of the SEF fits and the Kirchoff stresses through time for the results shown in FIGS. 13A-16C for two consecutive acquisitions to show the muscle, $S_{\theta\theta}$.
Figure 17F:
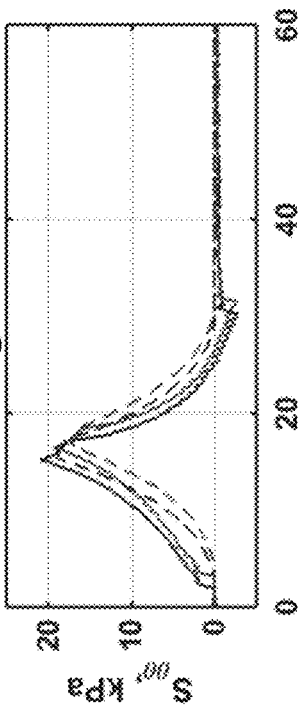
FIG. 17F is a graph showing examples of the SEF fits and the Kirchoff stresses through time for the results shown in FIGS. 13A-16C for two consecutive acquisitions to show the muscle, $S_{zz}$.
Figure 17A:
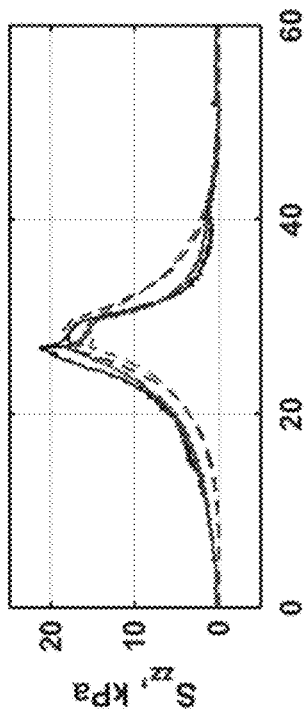
FIG. 17A is a graph showing examples of the SEF fits and the Kirchoff stresses through time for the results shown in FIGS. 13A-16C for two consecutive acquisitions to show the composite, $S_{\theta\theta}$.
Figure 17B:
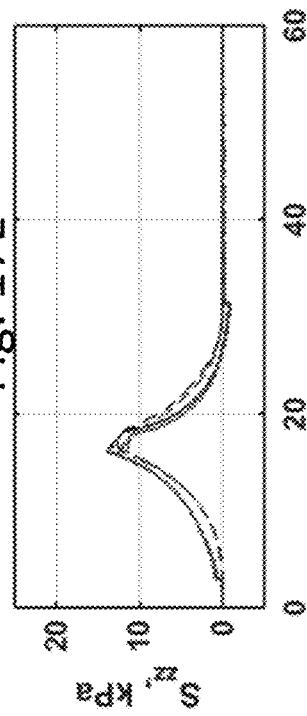
FIG. 17B is a graph showing examples of the SEF fits and the Kirchoff stresses through time for the results shown in FIGS. 13A-16C for two consecutive acquisitions to show the composite, $S_{zz}$.
Figure 17C:
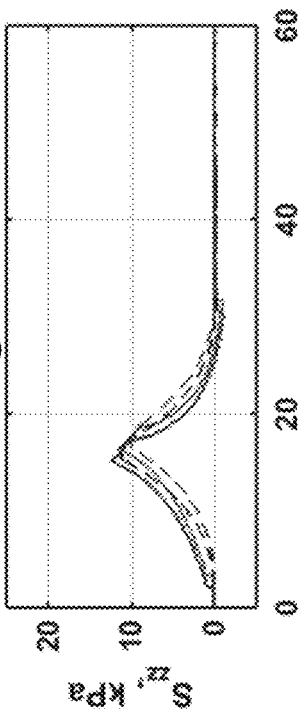
FIG. 17C is a graph showing examples of the SEF fits and the Kirchoff stresses through time for the results shown in FIGS. 13A-16C for two consecutive acquisitions to show the mucosa-submucosa, $S_{\theta\theta}$.

FIGS. 17A-17F provide graphs showing examples of the SEF fits and the Kirchoff stresses through time for the results shown in FIGS. 13A-16C for two consecutive acquisitions. All solid lines are the measured data and the dashed lines are the SEF fits. FIG. 17A shows data for composite, $S_{\theta\theta}$. FIG. 17B shows data for composite, $S_{zz}$. FIG. 17C shows data for mucosa-submucosa, $S_{\theta\theta}$. FIG. 17D shows data for mucosa-submucosa, $S_{zz}$. FIG. 17E shows data for muscle, $S_{\theta\theta}$. FIG. 17F shows data for muscle, $S_{zz}$.

Tables 4-6 summarize the parameter values found using the SEF fits along with the rms values to evaluate the goodness of the fits for five different esophagi samples for the composite, mucosa-submucosa, and muscle configurations, respectively. All reported values are mean±standard deviation for the repeated acquisitions for each sample.

TABLE 4

Summary of SEF fit parameters and rms values for composite esophagus samples.

| Sample | C, kPa | $a_{11}$ | $a_{22}$ | $a_{12}$ | rms $S_{\theta\theta}$, kPa | rms $S_{zz}$, kPa |
|---|---|---|---|---|---|---|
| 1 | 16.72 ± 1.62 | 3.46 ± 0.12 | 56.59 ± 35.08 | 3.71 ± 0.16 | 1.99 ± 0.12 | 2.02 ± 0.09 |
| 2 | 22.83 ± 3.76 | 2.88 ± 0.32 | 9.05 ± 0.96 | 2.99 ± 0.31 | 1.61 ± 0.39 | 1.49 ± 0.36 |
| 3 | 18.34 ± 3.73 | 1.31 ± 0.07 | 0.10 ± 0.00 | 1.67 ± 0.09 | 1.89 ± 0.39 | 2.65 ± 0.54 |
| 4 | 56.06 ± 3.76 | 0.48 ± 0.03 | 0.10 ± 0.00 | 0.66 ± 0.04 | 0.63 ± 0.07 | 0.88 ± 0.10 |
| 5 | 72.80 ± 18.03 | 0.67 ± 0.08 | 0.10 ± 0.00 | 0.85 ± 0.11 | 1.39 ± 0.74 | 1.79 ± 0.91 |

TABLE 5

Summary of SEF fit parameters and rms values for mucosa-submucosa esophagus samples.

| Sample | C, kPa | $a_{11}$ | $a_{22}$ | $a_{12}$ | rms $S_{\theta\theta}$, kPa | rms $S_{zz}$, kPa |
|---|---|---|---|---|---|---|
| 1 | 0.59 ± 0.32 | 0.48 ± 0.33 | 0.10 ± 0.00 | 0.41 ± 0.29 | 0.75 ± 0.02 | 0.44 ± 0.01 |
| 2 | 0.11 ± 0.01 | 3.28 ± 0.36 | 0.10 ± 0.00 | 2.73 ± 0.31 | 1.25 ± 0.04 | 0.74 ± 0.02 |

TABLE 5-continued

Summary of SEF fit parameters and rms values for mucosa-submucosa esophagus samples.

| Sample | C, kPa | $a_{11}$ | $a_{22}$ | $a_{12}$ | rms $S_{\theta\theta}$, kPa | rms $S_{zz}$, kPa |
|---|---|---|---|---|---|---|
| 3 | 0.11 ± 0.01 | 5.97 ± 0.84 | 0.10 ± 0.00 | 4.73 ± 0.66 | 1.56 ± 0.11 | 0.88 ± 0.06 |
| 4 | 0.49 ± 0.23 | 3.03 ± 1.34 | 0.10 ± 0.00 | 2.28 ± 1.01 | 1.75 ± 0.07 | 0.91 ± 0.04 |
| 5 | 0.16 ± 0.01 | 2.97 ± 0.28 | 0.10 ± 0.00 | 2.42 ± 0.22 | 1.33 ± 0.06 | 0.77 ± 0.03 |

TABLE 6

Summary of SEF fit parameters and rms values for muscle esophagus samples.

| Sample | C, kPa | $a_{11}$ | $a_{22}$ | $a_{12}$ | rms $S_{\theta\theta}$, kPa | rms $S_{zz}$, kPa |
|---|---|---|---|---|---|---|
| 1 | 0.21 ± 0.07 | 1.55 ± 0.47 | 0.10 ± 0.00 | 1.26 ± 0.39 | 1.60 ± 0.08 | 0.94 ± 0.04 |
| 2 | 0.10 ± 0.02 | 3.18 ± 0.96 | 0.10 ± 0.00 | 2.65 ± 0.79 | 1.19 ± 0.03 | 0.71 ± 0.01 |
| 3 | 0.99 ± 0.58 | 0.47 ± 0.58 | 0.10 ± 0.00 | 0.41 ± 0.49 | 1.22 ± 0.03 | 0.70 ± 0.01 |
| 4 | 0.71 ± 0.41 | 2.13 ± 1.71 | 0.10 ± 0.00 | 1.64 ± 1.32 | 1.92 ± 0.08 | 1.02 ± 0.05 |
| 5 | 0.05 ± 0.02 | 30.03 ± 2.05 | 0.86 ± 1.69 | 24.44 ± 1.66 | 1.56 ± 0.06 | 0.91 ± 0.04 |

The C values were much higher in the composite samples compared to the mucosal and muscular samples. We also observed variation among the different samples for a given configuration. One aspect of the fitting that was found is that the $\alpha_{22}$ value was set to a minimum value of 0.1 and often returned that limiting value, which indicated an insensitivity to the $E_{zz}$ values that it modifies. The rms values for the SEF fits were on the same order for the samples with mean values ranging from 0.44-2.66 kPa.

Using strain energy functions would have significant utility in determination of behavior under stress for structures which the thin walled assumption of structure is not valid and must be instead modeled as a thick walled tube. This has implications for testing GI system organs (thick walled) compared to selected vascular structures (variably thin walled tubes). While approaches such as optical tracking may be useful for ex vivo structures, in vivo approaches to monitor strain can be difficult and not feasible to be performed in vivo using optical tracking methods.

In summary, the above-described, non-destructive biaxial measurements compare favorably with other investigations of esophageal mechanics despite differences in species, testing methodology and modeling approach. The results from testing demonstrate that biaxial mechanical properties of excised esophagus may be reproducibly determined using piezoelectric elements and sonometry. Determination of biaxial mechanical properties in a non-destructive manner may allow for in vivo approaches for assessment and diagnosis of esophageal motility disorders as well as biomechanical quantification of tissue engineered constructs for esophageal replacement.

A strong advantage of the methods employed in this example is the nondestructive nature of evaluating the intact esophagus or individual layers. Other mechanical testing approaches currently used are destructive and only use a small portion of the sample. The results of a non-destructive approach may be used for future modeling of the biomechanics of the esophagus under varied conditions.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for measuring mechanical properties of a biological tube extending along an axis comprising:
    a tubular substrate dimensioned to extend along the axis of the biological tube and engage the biological tube;
    an array of piezoelectric elements engaging the tubular substrate;
    a pressure device configured to apply a predetermined force or transduce an endogenous or exogenous force to the biological tube and be sensed by the array when the array is engaged with the biological tube, wherein each piezoelectric element is configured to generate a signal in response to sensing application of the predetermined or transduced force; and
    a processor configured to receive the signal from at least two piezoelectric elements of the array and calculate a mechanical property of the biological tube based on signals received from the at least two piezoelectric elements in the array;
    wherein the tubular substrate is hollow and includes a lumen configured to receive the biological tube.

2. The system of claim 1, wherein the signal received from the at least two piezoelectric elements in the array include data related to a position of each of the piezoelectric elements within the array.

3. The system of claim 1, wherein the signal includes at least one of sinusoidal signal and coded signal.

4. The system of claim 1, wherein the processor is configured to apply a filter in order to condition the signal.

5. The system of claim 1 wherein the processor is configured to apply a matched or mismatched filter for processing the signal.

6. The system of claim 1, wherein the processor is configured to use upsampling and normalized cross-correlation to calculate a time-of-flight between a transmit and a receive indication in the signal.

7. The system of claim 1, wherein the piezoelectric elements in the array are configured to transmit signals at different time offsets selected to control signal interference.

8. The system of claim 1, wherein the processor is configured to use a model to compute anisotropic or isotropic material properties of the tubular substrate.

9. The system of claim 8, wherein the processor is configured to use the model to calculate anisotropic moduli.

10. The system of claim 8, wherein the model includes a plurality of different constitutive models, a fitted model, curve fitting modeling, or a combination thereof.

11. The system of claim 8 wherein the processor is further configured to select at least one of a model for a thick walled tubular structure and a model for a thin walled tubular structure.

12. The system of claim 8, wherein the processor is further configured to determine changes in distances between piezoelectric elements in the array based on the signal and use the changes in the distance as inputs to the model.

13. The system of claim 1, wherein the biological tube is one of a section of a gastrointestinal tract, an artery, and a vein.

14. The system of claim 1, wherein each piezoelectric element in the array is configured to be moved relative to the tubular substrate to reconfigure the array of piezoelectric elements.

15. A method for measuring a mechanical property of a biological tube, the method comprising:
    arranging a plurality of piezoelectric elements about the biological tube;
    applying a predetermined force or transducing an endogeneous or exogenous force applied to the biological tube;
    receiving a respective signal from each piezoelectric element in the plurality of piezoelectric elements responsive to the application of the predetermined or transduced force;
    calculating the mechanical property or mechanical properties of the biological tube based on the signals received from the plurality of piezoelectric elements; and
    determining changes in a distance between each piezoelectric element in the plurality of piezoelectric elements and calculating the mechanical property using the change in distance.

* * * * *